(12) United States Patent
Verma

(10) Patent No.: US 10,945,951 B2
(45) Date of Patent: Mar. 16, 2021

(54) APPARATUS FOR COMPOUND DISPERSION

(71) Applicant: Biogen MA Inc., Cambridge, MA (US)

(72) Inventor: Ajay Verma, Needham, MA (US)

(73) Assignee: Biogen MA Inc., Cambridge, MA (US)

( * ) Notice: Subject to any disclaimer, the term of this patent is extended or adjusted under 35 U.S.C. 154(b) by 256 days.

(21) Appl. No.: 15/536,508

(22) PCT Filed: Dec. 17, 2015

(86) PCT No.: PCT/US2015/066240
§ 371 (c)(1),
(2) Date: Jun. 15, 2017

(87) PCT Pub. No.: WO2016/100591
PCT Pub. Date: Jun. 23, 2016

(65) Prior Publication Data
US 2017/0360699 A1 Dec. 21, 2017

Related U.S. Application Data

(60) Provisional application No. 62/094,265, filed on Dec. 19, 2014.

(51) Int. Cl.
*A61K 9/00* (2006.01)
*A61H 9/00* (2006.01)
*A61H 23/02* (2006.01)
*A61H 31/00* (2006.01)
*A61H 23/00* (2006.01)

(52) U.S. Cl.
CPC ............ *A61K 9/0085* (2013.01); *A61H 9/00* (2013.01); *A61H 9/005* (2013.01); *A61H 9/0078* (2013.01); *A61H 9/0092* (2013.01); *A61H 23/00* (2013.01); *A61H 23/0245* (2013.01); *A61H 31/00* (2013.01); *A61K 9/0019* (2013.01); *A61H 2201/0103* (2013.01); *A61H 2201/0149* (2013.01); *A61H 2201/165* (2013.01); *A61H 2201/1619* (2013.01); *A61H 2201/5002* (2013.01); *A61H 2205/08* (2013.01)

(58) Field of Classification Search
CPC ............ A61K 9/0085; A61M 25/003; A61M 25/0021; A61M 25/0023
See application file for complete search history.

(56) References Cited

U.S. PATENT DOCUMENTS

| 8,801,591 | B1* | 8/2014 | Lasorso, Jr. | ........... A61H 1/005 600/28 |
| 2005/0020945 | A1 | 1/2005 | Tosaya et al. | |
| 2005/0137578 | A1* | 6/2005 | Heruth | .............. A61M 5/14276 604/536 |
| 2006/0161200 | A1 | 7/2006 | Fallah | |
| 2007/0167887 | A1 | 7/2007 | Tsukada et al. | |
| 2009/0069728 | A1* | 3/2009 | Hoffmann | ................ A61N 7/00 601/46 |
| 2012/0003202 | A1* | 1/2012 | Calias | .................. A61K 9/0085 424/94.3 |
| 2013/0131558 | A1 | 5/2013 | Lee | |

FOREIGN PATENT DOCUMENTS

WO     WO 02/06673 A1     1/2002

OTHER PUBLICATIONS

Mardor et al (Convection-Enhanced Drug Delivery: Increased Efficacy and Magnetic Resonance Image Monitoring; Cancer Res 2005; 65 (15), 2005) (Year: 2005).*
International Search Report and Written Opinion for International Application No. PCT/US2015/066240, dated Mar. 24, 2016, 16 pages.

* cited by examiner

*Primary Examiner* — Micah Paul Young
(74) *Attorney, Agent, or Firm* — Wolf, Greenfield & Sacks, P.C.

(57) ABSTRACT

Methods and apparatuses for dispersing a compound within the patient are described. In one embodiment, an effective amount of a compound may be present in the cerebrospinal fluid of a patient and a force may be applied to the torso of the patient sufficient to enhance the convection of the cerebrospinal fluid. In another embodiment, a bolus including a compound may be injected into the cerebrospinal fluid of a patient. The volume of the bolus may be between about 5% and 30% of the total volume of the cerebrospinal fluid of the patient.

43 Claims, 18 Drawing Sheets

*Non-Cell penetrating probe*
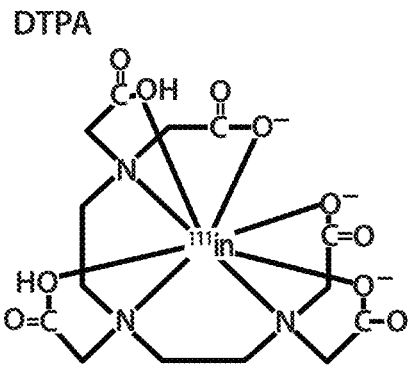
*Mitochondria targeting probe*
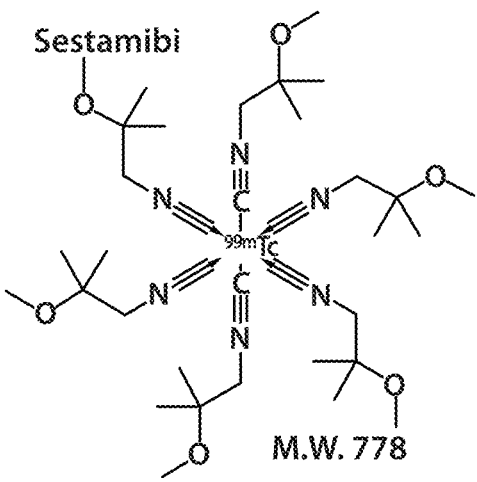
Fig. 8A
Fig. 8B
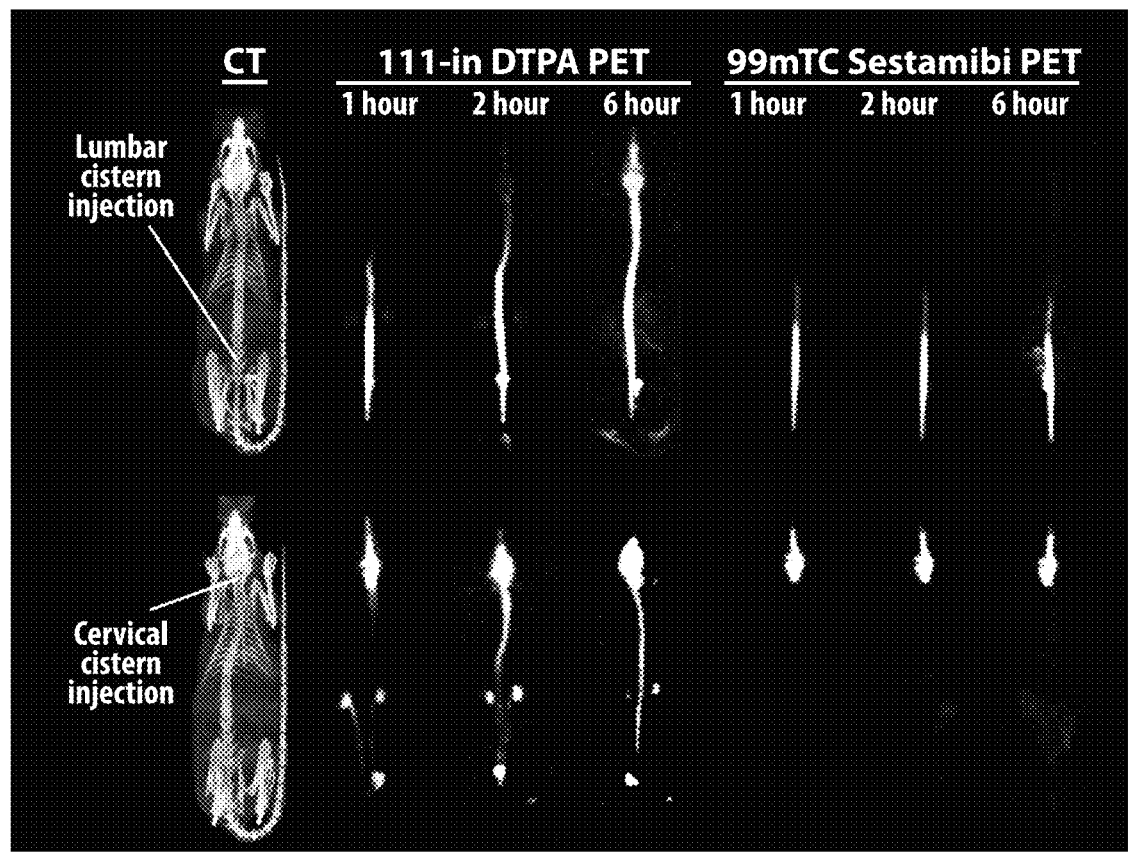
Fig. 8C Cisternal Injections 6 hours

*IT Injections*

*6 hours*

APPARATUS FOR COMPOUND DISPERSION

FIELD

Disclosed embodiments are related to methods and apparatuses for compound dispersion.

BACKGROUND

Intrathecal compound delivery may be used to bypass the highly impermeable blood brain barrier (BBB) and allow compounds to directly access targets in the central nervous system (CNS). However, intrathecal therapy is known to display high inter-patient variability as well as caudal to rostral exposure gradients across different CNS structures. Lumbar administration is the most commonly used intrathecal injection approach and typically results in high compound exposure to the lumbar spinal cord with a decreasing gradient of exposure to the thoracic and cervical cord. Rostral brain structures within the skull display lesser and more variable exposure after lumbar intrathecal injection than the thoracic and lumbar cord due to this concentration gradient. Additionally, deep brain structures such as the basal ganglia, thalamus and cerebellar nuclei show the lowest exposure for this type of compound delivery. Without wishing to be bound by theory, the observed gradient may be the result of a combination of factors including the rate of cerebrospinal fluid (CSF) circulation, affinity of a given compound for CNS tissue or meninges, as well as the clearance of the compound from the CSF space to the plasma.

SUMMARY

In one embodiment, a method for dispersing a compound within the intrathecal neuraxis of a patient includes: applying a force to a torso of a patient to enhance convection of cerebrospinal fluid including an effective amount of a compound to enhance dispersion of the compound.

In another embodiment, a method for dispersing a compound within a patient includes: injecting a bolus including a compound into cerebrospinal fluid of a patient. A volume of the bolus may be between or equal to about 5% and 30% of a total volume of the cerebrospinal fluid of the patient.

In yet another embodiment, a method for dispersing a compound within a patient includes: applying a force to a torso of a patient to enhance convection of lymph including an effective amount of a compound contained in the lymph node to enhance dispersion of the compound.

In another embodiment, a device for dispersing a compound within a patient includes an element constructed to apply a force to a torso of a patient. A peak magnitude, force gradient, frequency, wave form, and/or and wave/pause sequence of the force is selected to enhance convection of the cerebrospinal fluid of the patient.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 8A is a schematic representation of a non-cell penetrating probe;

FIG. 8B is a schematic representation of a mitochondria targeting probe;

FIG. 8C presents SPECT scan images at different time points for an lumbar cistern and cervical cistern injection in a rat including the probes depicted in FIGS. 8A and 8B;

DETAILED DESCRIPTION

Figure 1:
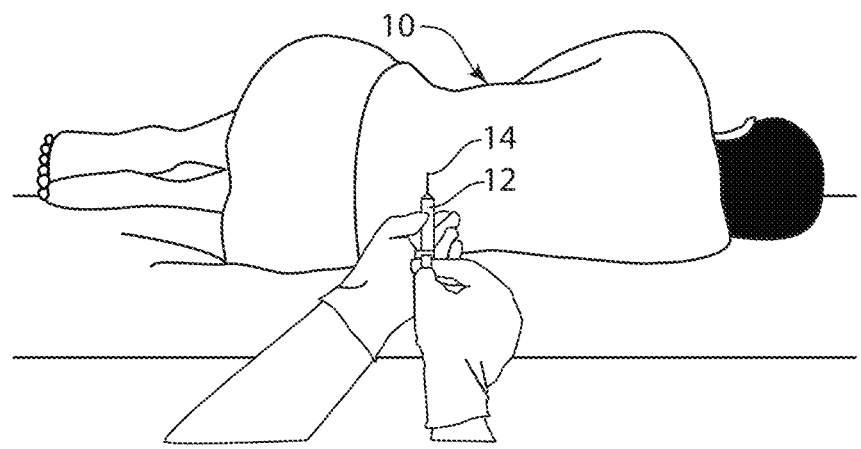
FIG. 1 is a schematic representation of intrathecal compound injection into a patient.

Cerebrospinal fluid (CSF) is a clear, colorless fluid that bathes the entire surface of the central nervous system (CNS). CSF is normally produced within the ventricles of the brain and exits through specific channels to bathe the surface of the entire neuraxis (nerve roots, spinal cord, brainstem, cerebellum, and cerebrum). The neuraxis is typically defined as all CNS structure enclosed within the meninges, including nerve roots, spinal cord, brainstem, cerebellum and cerebrum. The CSF bathing the surface of the neuraxis is contained within the connective tissue coverings known collectively as the meninges. The meninges are composed of three layers: the dural layer is adherent to the skull and vertebrae; the pia layer is adherent to the brain and spinal cord; and the arachnoid layer lies in between the dura and pia layers. CSF largely resides between the pia and arachnoid layers, a space referred to as the subarachnoid space. This space has a unique anatomy with regionally variable volume and shape characteristics along the neuraxis. Various locations along the neuraxis exhibit increased regional separations between the pia and arachnoid meningeal layers which create widened spaces, called cisterns, which contain greater CSF volume than other areas along the neuraxis. These cisterns are oftentimes used as injection points for delivering a bolus into the CSF for distribution of various compounds along the CNS of a patient.

Typically a young adult human has a total CSF volume of about 150 ml. However, the total CSF volume may vary drastically between individuals and may be as small as 100 ml and as large as 500 ml. In a representative example, for a total volume of 150 mL within a human, about 25 ml resides in the ventricles of the brain while the remaining 125 ml resides in the cranial and spinal subarachnoid space. CSF is produced at a rate of about 0.3 ml/minute to 0.4 ml/minute or about 400-600 ml/day. Consequently, the CSF for a representative person typically turns over completely about 4 times a day. In addition to the above, the total CSF volume in adolescents typically varies between about 125 ml and 150 ml and in children between about 60 ml and 150 ml. While typical CSF volumes for humans are noted above, it should be understood that the current disclosure is also applicable to other vertebrates as well. For example, therapies for animals using intrathecally injected compounds may benefit from the current disclosure and lab animals may be subjected to the various techniques and devices disclosed herein during drug validation trials.

Compounds for purposes of this application may correspond to any appropriate material including, but not limited to, any diagnostic compound, tagged compound, therapeutic compound, and combination thereof such as a drug, medication, pharmaceutical tracer, contrast agent, and/or biologics such as proteins, antisense molecules, and gene therapy viral vectors as the disclosure is not so limited. Therefore, depending on the embodiment, the methods and devices described herein may be used to aid in the delivery of a compound including one or more therapeutic compounds, one or more diagnostic compounds, combinations of one or more diagnostic compounds and one or more therapeutic compounds, or combinations of any other desirable compounds as the disclosure is not limited to the delivery of any particular compound or combination of compounds. It should also be understood that the specific amount and effect will vary depending on the particular compound being used. Additionally, as will be appreciated by one of skill in the art, the compounds described herein may be provided in any number of different forms including, but not limited to, suspensions, liquids, slurries, powders, nanoparticles, and/or gels.

The above noted compounds may be present within the CSF and/or lymph of a patient, and/or at a particular target site of the CNS of the patient, in an effective amount. The term "effective amount" means an amount of a compound, that is greater than or equal to a trace amount, and that is sufficient for achieving a desired purpose, such as, for example, to permit detection of the compound in a subject for diagnostic purposes and/or to treat a disease or condition in a subject. In some embodiments, an effective amount of a particular therapeutic compound (e.g., analgesic small molecule or peptide; monoclonal antibody, antisense oligonucleotide, gene therapy viral vector) is present in an amount sufficient to reduce or alleviate one or more conditions associated with a particular condition (e.g., Neuropathic pain, primary brain or metastatic cancer, neurodegenerative disease, neurogenetic disease, neuro-infections disease). In another embodiment, an effective amount of a particular diagnostic compound (e.g., a compound conjugated with detectable moiety such as a radioisotope) is present in an amount sufficient to detect the compound in the subject for diagnostic purposes using an appropriate detection modality (e.g., a PET, SPECT or MRI scanner).

Compounds can be introduced into the cerebrospinal fluid (CSF) via injection into the cerebrospinal fluid at any level of the neuraxis, such as at the ventricles, the cervical cistern space, or the lumbar cistern space. Lumbar cistern injection is the most commonly used CSF dosing route. However, as noted above, this dosing route typically produces a compound concentration gradient with the lumbar region exhibiting the highest concentration and the more rostral regions exhibiting much lower concentrations. Consequently, intrathecal lumbar therapy is typically used for treating conditions affecting the lower spinal cord and nerve roots for conditions such as leg and back pain or spasticity. Given the ease of access to the CSF space via the lumbar cistern, this route is also used for compound delivery to the higher spinal cord, brainstem, and brain regions, but requires higher doses and/or the use of catheters advanced into the neuraxis of a patient. However, the use of higher doses may result in local toxicity, and the use of catheters may result in mechanical complications.

In view of the above, the inventors have recognized that dispersing a compound more effectively within the CSF of a patient may help to lower the localized concentrations of a compound, thus reducing possible local toxicity, and provide therapeutic benefits to other more rostral regions of the central nervous system (CNS). More specifically, the inventors have recognized that enhancing the convective movement of CSF within a patient results in faster dispersion of compounds along the CNS resulting in reduced concentration gradients. For example, applying a force to a torso of the patient using an external source of mechanical energy may be used to increase the convection, and thus distribution, of a compound within the CSF of a patient. In other embodiments, the use of larger bolus volumes may be used to aid in the enhanced distribution of a compound within the CSF of a patient. Additionally, sources of endogenous convection forces such as cardiac activity and respiration may also help with dispersing compounds in the CSF. Therefore, in some embodiments, increasing the heart rate and/or a respiratory rate of a patient may be used to increase the convection, and thus distribution of a compound within the CSF of a patient. The above noted embodiments may be used separately, or in combination, to promote distribution of a compound within the CSF of a patient.

The methods described herein may aid in more uniformly dispersing compounds along a neuraxis of a patient when they are injected directly into the CSF of a patient such that the compound dispersion may be more robust and reach deeper into the CNS of a patient. This type of approach may help to reduce the caudal to rostral gradient typically seen with this type of dosing approach and may allow the exposure of compounds to desired CNS structures within the upper spine and skull vault and other applicable portions of the CNS. It should be understood that while particular treatments are described herein, the presently described methods and apparatuses are generally applicable and should not be limited to only the particular therapy or injection site as the disclosure is not so limited.

While a generic force applied to the torso, or other portion of a patient's body has been described, it should be understood that different types of forces may be used in different embodiments. For example, in one embodiment, a static force is applied to one or more portions of a patient's body. In another embodiment, a dynamic time varying force that varies in magnitude, frequency, location, wave form, and or wave/pause dynamics may be applied instead. Additionally, both static and dynamic forces may include force gradients that are applied across different portions of a patient's body. Therefore, while generic forces are described herein for convenience and clarity sake, it should be understood that both dynamic and static forces may be applied to any of the embodiments described herein.

Having generally described several methods for enhancing CSF convection within a person to aid in the dispersion of a compound, several more detailed embodiments are described below. However, it should be understood that the various embodiments are not exclusive from one another and may either be used separately or combined as desired since the disclosure is not so limited.

In one embodiment, a bolus including a compound is injected into the cerebrospinal fluid of a patient in an effective amount. A force may then be externally applied to a torso of the patient. Without wishing to be bound by theory, this externally applied force may result in convection of CSF within the patient, which results in additional mobility and dispersion of the compound injected into the CSF. One or more of a peak magnitude, total force change, frequency, wave form, wave and/or pause sequence, multiple waves or any other appropriate variable of the force may be selected to provide a desired degree of increase in the convection of the cerebrospinal fluid relative to the normal amount of cerebrospinal fluid convection. Without wishing to be bound by theory, it is believed that pressure waves transferred into the CSF as well as compression and decompression of the various structures of the CNS may result in the observed enhanced convection of the CSF and resulting enhanced dispersion of compounds.

A force may be applied to a torso of a patient using any appropriate device capable of applying mechanical forces, such as percussive or vibrational forces (i.e. fast impulses), pressing forces (i.e. time varying quasi static forces applied to a surface of the torso), constriction around the torso, and/or shear forces to the torso of a patient with a desired peak magnitude, total force change, and frequency. Appropriate force application elements include, but are not limited to: displaceable plates; displaceable rollers; inflatable bladders; vibrating elements (mechanical, electromechanical, piezoelectric, etc.); tethers, straps, and cords attached to a structure such as a vest capable of being pulled on to apply a compressive force to the torso; as well as any other component capable of applying a mechanical force to the torso of a patient. The force application element may be driven using any appropriate drive system including, but not limited to, a pneumatic energy source, a pump or other hydraulic energy source, an electromechanical motor system, contracting/expanding materials such as shape memory alloys and polymers or electroactive polymers, and/or an electric drive (piezoelectric, solenoids, etc.). Several non-limiting examples of devices and methods that may be used to provide the desired force to a patient's torso include, but are not limited to, a mechanical vest, a pneumatic vest, a vibrating chair, physical therapy/message, ultrasound transducers or any other appropriate method or device capable of enhancing the convective movement of compounds in cerebrospinal fluid (CSF).

Depending on the embodiment, a force may be applied to the torso of a patient in a number of different locations. For example, the force may be applied: along a length and about a circumference of a torso at the same time (e.g. as might happen in a constrictive vest); to different locations of the torso at different times; and/or to only a portion of the torso as the disclosure is not so limited. The force may be directed, for example in a caudal to rostral direction. The forces applied to these separate locations may either exhibit the same or different peak magnitudes, total force changes, and/or frequencies, wave forms or wave/pause sequences as the disclosure is not so limited. Therefore, it should be understood that the forces may be applied to any appropriate location and portion of the torso of a patient as the disclosure is not so limited.

As noted previously, a device may apply mechanical forces to a torso of a patient in any number of ways. For example, in one embodiment, a device may apply forces to the torso of a person in a normal direction. In other embodiments where a shear force is applied to a person's torso, first and second shear forces applied to the torso during a cycle of the device may be applied in opposing directions. In other words, in some embodiments, the device may apply forces in opposite directions to the torso as it vibrates back and forth. Of course embodiments in which both normal and shear forces are applied to a person's torso are also contemplated.

The peak magnitudes, total force change, direction, frequency, wave form and wave/pause sequence of a force applied to a person's torso may be provided in any desirable way. For example, the force may be applied as sharp impulses where the force is simply applied and removed quickly somewhat similar to a square waveform. Alternatively, the force may vary continuously between at least two forces using a continuous or semi continuous waveform. For example, the force may transition between two or more forces as detailed above. Though it should be understood that the disclosure is not limited to any specific number or type of force waves.

Depending on the particular device, compound, and therapy being used, a peak magnitude of a force applied to a person's chest may range between about 0 and 1 psi, 0.5 psi to 1 psi, or any other applicable pressure range. Additionally, a minimum force applied to the torso of a person by the device may either be zero, or it may be greater than zero and less than the peak magnitude. In one embodiment, the minimum force may be between about 0 psi and 0.9 psi, 0.1 psi and 0.5 psi, 0.5 psi and 0.9 psi, or any other appropriate pressure range. For example a maximum peak force corresponding to an applied pressure of 1 psi and a minimum peak force corresponding to an applied pressure of 0 psi would result in a total force change corresponding to about 1 psi. However, other appropriate total force changes corresponding to applied pressure changes between about 0.1 psi to 1 psi, 0.1 psi to 0.5 psi, and 0.5 psi to 1.0 psi are also contemplated as the disclosure is not limited to any particular range of pressures. In addition to the force magnitudes, dynamically applied forces may be applied using a frequency range between about 5 Hz to 25 Hz, 10 Hz to 25 Hz, or any other applicable frequency range as the disclosure is not so limited. While the above noted embodiment is directed to the use of a dynamically applied time varying force, embodiments in which a static force is applied using the above noted pressure ranges are also contemplated.

In another embodiment, it may be desirable for a device to apply mechanical forces to a torso of a patient in a particular direction, or combination of directions. For example, a force may be applied substantially normal to a torso of a patient to provide a compressive force to the torso. Alternatively, in another embodiment, the force may be applied laterally relative to a surface of the torso of a patient such that it imposes a shear force to the torso as compared to a compressive force. This laterally oriented force may either be directed towards the head, feet, sides, or combination of the above. In yet another embodiment, a device may apply a force to a torso of a patient that includes components both in the normal and lateral directions relative to a surface of the torso of the patient. Alternatively, the device may alternate between applying a normal and shear force to the torso of the patient. In some embodiments a static force is used that includes a gradient that increases in one direction so as to direct the distribution of a compound away from the highest force. For example, a static force may have a gradient such that the force increases in the caudal to rostral direction, though other gradient directions are also contemplated. In another embodiment, a static non-directed force is applied so as to assist in the dispersion of a compound towards areas of lower force. Without wishing to be bound by theory, applying a non-uniform pressure to a patient's torso may induce a flow of cerebrospinal fluid towards areas of lower pressure thus aiding the dispersion of compounds along the neuraxis of a patient.

In some instances, it may be desirable to provide a force to various portions of a patient's torso in sequence to further aid in the convective flow of CSF in a particular direction within a neuraxis of a patient. For example, a force may be applied to a first location such as the injection site. The force may then either move in a desired direction towards a desired target site, or the force may be removed from the first location and a force applied in a second location located closer to the desired target site. These forces at the different locations may either be applied sequentially (i.e. the force is removed from the first location prior to applying it to the second location), or the force may be applied at the second location prior to removing the force at the first location. This sequence may continue for any number of locations such that the forces are applied sequentially to a plurality of locations on the torso of a patient. In either case, movement of the force's location, and/or the sequential application of forces in different locations, may help to facilitate convective movement in the CSF towards a desired target location.

One non-limiting embodiment of a device capable of operating in the above noted fashion is a vest including multiple pneumatically or mechanically controlled sections that apply a compressive or constructive force to a plurality of portions of a torso. These sections may be actuated in sequence to apply a force to a lower portion of the torso first and then an upper portion of the torso last such that the applied forces move up the torso. These forces may be applied cyclically such that after the force is applied to the upper portion of the torso the cycle is begun again and a force is applied to a lower portion of the torso. It should be understood that the forces may also be applied in the reverse direction moving from an upper portion of the torso to a lower portion of the torso as well since the disclosure is not so limited. Therefore, the above embodiment should be interpreted generally as sequentially applying forces in different locations along a torso to enhance the convection of CSF towards a desired target location in any appropriate direction using any appropriate device. In one embodiment, an appropriate device may include, or be similar to, a sequential compression device such as those used in the treatment of deep venous thrombosis and pulmonary embolisms.

While embodiments have been described with forces being applied to different locations on a torso of a patient, it should be understood that a force may simply be applied at the same location. For instance, in one embodiment, a force may be applied to a single portion of a torso or a force may be applied to the entire torso of a patient as the disclosure is not so limited. Transmission of convective force to the CSF may also be achieved by applying a force to the hips, sacrum, or legs using an appropriate mechanical device. Appropriate devices include, but are not limited to, vests, belts, vibrating beds, vibrating platforms upon which an individual can stand, or other appropriate devices that are capable of applying mechanical forces, thermal energy, subsonic energy, sonic energy, ultrasonic energy, or combinations thereof to optimally disperse a compound within the CSF or lymph of a patient.

In another embodiment, transmission of convective force to the CSF may be achieved by application of force internally via the respiratory tract. Several such devices used clinically for clearing airways in respiratory disorders may be adapted to serve this purpose. For example, in one embodiment, oral high frequency oscillation (OHFO) introduces high frequency and low volume oscillations into the breathing of a patient. These oscillations do not hinder the spontaneous breathing of the patient and the technique has potential value as a supplement to ventilation. Sine wave oscillations are produced by an eccentric cam piston and can be superimposed on normal tidal breathing. The low volumes of approximately 50 ml and pressures approximately 0.2 cm-2.0 cm H2O with a mean pressure of zero can allow subjects to breathe spontaneously while still transmitting convective force to the CSF space. In another embodiment, intrapulmonary percussive ventilation (IPV) combines aerosol inhalation and internal thoracic percussion applied via a mouthpiece. The IPV is the delivery of a pulsatile flow of gas released with each pulse that can be preset and the pulsation frequency can be adjusted to each individual. Likewise, handheld clearance devices that combine positive expiratory pressure therapy with high-frequency oscillations within the airway may also be used to introduce forces internally within the respiratory tract of a patient. In either case, these embodiments provide a controlled vibration system which produces positive expiratory pressure and cyclic oscillations of the airways during expiration which may either individually, or in combination with other techniques, enhance the convective forces present in the CSF.

A device may be used to apply a force to a patient's torso during and/or after the injection of a compound into the CSF of the patient. Additionally, the force may be applied for any appropriate amount of time to provide a desired amount of distribution of one or more compounds within the CSF of the patient. It should be understood that appropriate time durations will depend on the particular compound and solutions being used, treatment or procedure involved, as well as specifics about a particular patient being treated. However, in some embodiments, a force may be applied for between or equal to about 15 min to 60 min In another embodiment, a method to increase the distribution of an injected compound in the CSF of a patient is to inject a large volume bolus. Depending on the particular application, a bolus including one or more desired compounds, and in some embodiments, an appropriate carrier, may have a volume that is greater than or equal to about 5%, 10%, 15%, or any other appropriate percentage of the total volume of CSF of a patient. Additionally, the bolus volume may be less than or equal to about 30%, 20%, 15%, 10%, or any other appropriate percentage of the total volume of CSF of a patient. The above percentage ranges may be combined. For example, a bolus volume may be between or equal to about 5% and 30% of the total volume of CSF of a patient. In some instances, the volumes corresponding to the above percentages are determined on an individual basis for each patient. In such an embodiment, the total volume of CSF of a patient is measured using any appropriate method including, magnetic resonance imaging. After determining the total volume of CSF of a patient, the desired bolus volume is determined to provide a bolus with a volume between about 5% and 20% of the total CSF volume of that patient. Alternatively, in another embodiment, an average total CSF volume of about 150 mL for an average adult human may be assumed. In such an embodiment, a corresponding bolus volume between or equal to about 7.5 mL and 30 mL may be used.

Without wishing to be bound by theory, an optimal bolus volume for a given application will be dependent on a number of factors. For example the affinity of a compound for tissue within the CNS of a patient will affect how quickly the compound is absorbed into tissue, which will limit how far the compound can spread along the CNS. Therefore, larger volumes may be appropriate for compounds having higher tissue affinities in order to further enhance their distribution along the neuraxis prior to their local tissue adsorption. Additionally, compounds exhibiting toxicity above a certain concentration threshold may require the use of larger bolus volumes at lower concentrations and/or extended injection times to avoid local toxicity issues. There may also be effects associated with individual patients that will affect the distribution of a compound within the CSF of a patient. Due to these considerations, in some embodiments, appropriate bolus volumes, injections rates, and/or injection times may be found in a look up table for various types of compounds to aid a practitioner in selecting the appropriate bolus volumes for a particular application.

As noted above, compounds may be delivered in the form of a bolus, which may be a liquid bolus for example. A bolus may include various constituents including, but not limited to, the desired active compound or compounds, a suitable pharmaceutical excipient or carrier, and/or any other desired ingredient. For example, a bolus might include a desired compound suspended in a carrier solution. Boluses may also take the form of a gel, slurry, powder, particle suspension, combinations thereof, or any other appropriate form as the disclosure is not so limited. Appropriate compounds include, but are not limited to, small molecules, peptides, proteins such as antibodies and enzymes, oligonucleotides, gene therapy viral vectors and liposomes or other compound delivery vectors. Appropriate pharmaceutical excipients or carriers include, but are not limited to, saline and artificial CSF. It should be understood that the relative amounts of the active compounds, the pharmaceutically acceptable excipient or carrier, and/or any additional ingredients in a pharmaceutical composition will vary depending upon the identity, size, and/or condition of a patient being treated, the involved treatment or procedure, and further depending upon the route by which the composition is to be administered. Additionally, a solution may comprise any appropriate concentration including for example between about 0.1% and 100% (weight/weight) active compounds.

The above noted therapies may be used with various injection sites. For example, a solution may be injected into the cervical cistern, lumbar cistern, intracerebral ventricles, or intranasally, or any other appropriate location capable of injecting the solution into the CSF of a patient. For example, in some embodiments, a bolus of solution may be injected into a head and neck lymph node, tonsil, or lymphatic vessels of a patient. Due to the interconnectivity of these lymphatic structures and CSF located in the neuraxis, a solution injected into a lymph node may migrate into the CSF and vice versa. Additionally, similar to the above embodiments directed to injecting a compound directly into the CSF, applying a force to a torso of the patient with an appropriate peak magnitude, total force change, and frequency similar to those described above may increase the convection of lymph fluid contained in lymphatic vessels and lymph nodes. This may aid in dispersing the solution within the lymph node, migration into the CSF from the lymph node, and subsequent dispersion within the CSF. The force may also be used to increase the convection of lymph between separate lymph nodes. Other non-direct approaches for administering a compound into the intrathecal space are also contemplated as would be apparent to one of skill in the art.

In some embodiments, it may be desirable to determine whether or not a compound has reached a target site in a desired concentration. In such an embodiment, the compound, or another component of a solution such as the carrier solution, or a separate inert component, may include an appropriate marker. Appropriate markers include, but are not limited to, radioactive markers, radiopaque markers, near infrared fluorescent markers, luminescent markers and magnetically tagged markers to name a few. Any appropriate scanner or detecting device may be used to sense the presence of the marked compound, and in some embodiments measure the concentration of the marked component at a desired target site. Appropriate scanners/detectors include, but are not limited to, positron emission tomography scanners, mobile positron emission tomography scanners, gamma radiation detectors, computed x-ray tomography scanners, x-ray imagers, fluorescence and luminescence imagers, magnetic resonance imagers, and/or radiation detectors to name a few. Appropriate target sites that might be monitored include, but are not limited to, various portions of the neuraxis such as portions of the brain and spine, lymph nodes, oral and intranasal cavities and/or any other desired target site. For some conditions requiring chronic intrathecal therapy, miniature detectors and sensors may even be implanted inside the intrathecal space. In addition to the above, in some embodiments, intrathecal sensors may also used to sense and/or measure pressure, volume, flow and soluble analytes such as endogenous toxic molecules, therapeutics, neurotransmitters, and metabolites. Additionally, while the current disclosure has been described as being used with minimally invasive and non-invasive techniques, the disclosure may also be used with invasive monitoring and sampling techniques including, for example, withdrawing CSF from along the length of the neuroaxis to monitor the distribution of compounds.

The above noted sensors and detectors may either be used intermittently or continuously. For example, a scanner may determine the concentration of a desired compound and/or solution at a target site after a predetermined duration of a force being applied to the torso of a patient. Alternatively, the scanner may continuously monitor the concentration of a compound and/or solution at a target site. After sensing and measuring a concentration above a threshold concentration, the force may be ended or adjusted. Alternatively, if the measured concentration is below the desired concentration threshold, the force may be continued in order to facilitate further distribution of the compound. In some instances the measured concentration may be correlated to a number of counts per unit time or other appropriate measure correlated with the presence and concentration of a marked component of a solution.

In some embodiments, it may be desirable to further facilitate the distribution of a compound and/or solution along a neuraxis of a patient. Various methods which may be used include, but are not limited to, the local application of ultrasonic energy, sonic energy, subsonic energy, and/or thermal energy. In such an embodiment, one or more of these forms of energy may be externally applied on the back along a portion, or the entire length of, the spine to locally enhance the convection of CSF. Additionally, increased heart rates and respiratory rates may be used to enhance the convection of CSF. Therefore, methods of increasing heart rates and respiratory rates such as exercise, incentive spirometry and/or adrenaline, to name a few, might be used to further enhance convective distribution of a compound in the CSF of a patient. These methods may either be used individually or in any combination with the methods and apparatuses described herein directed to applying forces and larger bolus volumes to achieve a desired distribution of a compound within the CNS of a patient. Thus, for example, a respiratory vest, or other device, may include a heat or ultrasound source that applies heat or ultrasonic energy at one or more locations on an exterior of the torso corresponding to an appropriate portion of the CNS (e.g. along a length of the spine) in addition to a force.

As detailed further in the examples, and without wishing to be bound by theory, the molecular weight of a compound does not appear to significantly impact the distribution of the compound within the CSF of a patient. This distributing effect is believed to be due to convective mixing dominating the transport mechanisms of compounds located in the CSF. Therefore, the above noted methods of increasing the uniformity and distribution of compounds along the CNS of a patient may be used with both low molecular weight and high molecular weight compounds.

Turning now to the figures, several non-limiting embodiments and examples are described in more detail. It should be understood, that the various portions of the embodiments described in relation to the figures can be combined in any desired manner and the disclosure is not limited to only those specific embodiments described herein.

Figure 2:
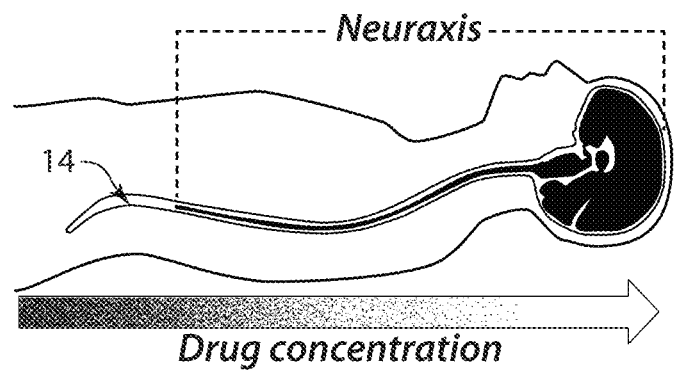
FIG. 2 is a schematic representation of the compound concentration along a neuraxis of a patient after intrathecal injection.
Figure 3:
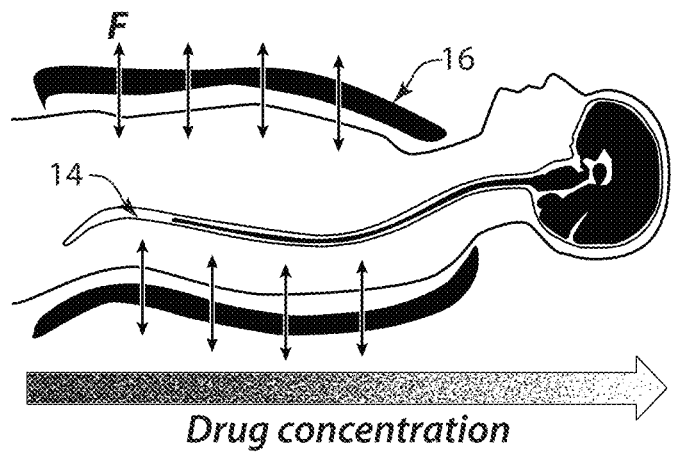
FIG. 3 is a schematic representation of the compound concentration along a neuraxis of a patient after intrathecal injection with a time varying force applied to a torso of the patient.

FIG. 1 illustrates a patient 10 receiving a bolus of solution 12 at injection site 14. In the depicted embodiment, the injection site is located at the lumbar cistern corresponding to an intrathecal injection. FIG. 2 illustrates the concentration gradient of the solution along a neuraxis of a patient after intrathecal injection at injection site 14. As can be seen in the figure, the concentration decreases from the injection site towards the upper portion of the neuraxis. As noted previously, this concentration gradient may lead to local concentrations of a compound above a cell toxicity threshold and/or may result in a compound not reaching a desired target. In contrast, FIG. 3 depicts the concentration gradient when a source 16 of a desired force F, which in this instance is a dynamic force, is applied to the torso of the patient. As described above, the forces applied to the torso result in enhanced convection of the CSF located within the neuraxis of the patient. Without wishing to be bound by theory, this enhanced convection of the CSF results in enhanced distribution of the compound between the injection site and the target site located along the neuraxis as illustrated by the arrow indicating a reduced drug concentration gradient. While the applied forces have been depicted as being normal to the torso of a patient, other orientations of the force relative to the torso, such as lateral to a surface of the torso to apply a shearing force, and combinations of normal and lateral forces are also contemplated.

Figure 4A:
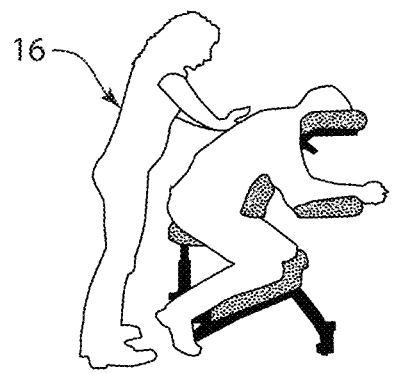
FIG. 4A is a schematic representation of a person massaging the torso of a patient.
Figure 4B:
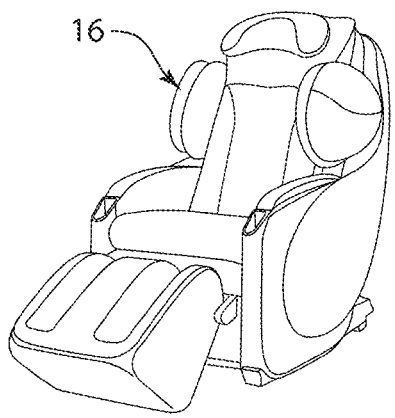
FIG. 4B is an image of a vibrating chair.
Figure 4C:
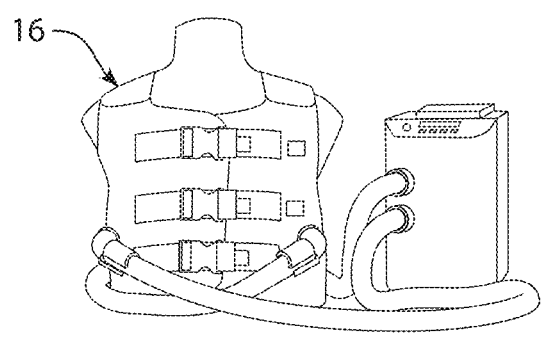
FIG. 4C is an image of a respiratory therapy vest.

It should be understood that any appropriate source for the forces may be used as depicted in FIGS. 4A-4C. For example, as illustrated in FIG. 4A forces may be manually applied to the torso of a patient via manual percussion and/or massage. In other embodiments, a vibrating chair or massage chair is used to apply the desired forces to a torso of a patient as shown in FIG. 4B. Alternatively, in another embodiment illustrated in FIG. 4C, a vest worn on the torso of a patient is used to apply the desired forces. For example, a pneumatic or hydraulic power source 16a may be used to inflate one or more bladders located within the vest to apply pressure to one or more locations on the torso of a patient. In this particular instance, the depicted vest is a respiratory therapy vest set to an appropriate magnitude and frequency useful for enhancing the convection of CSF within the neuraxis of a patient.

Figure 5A:
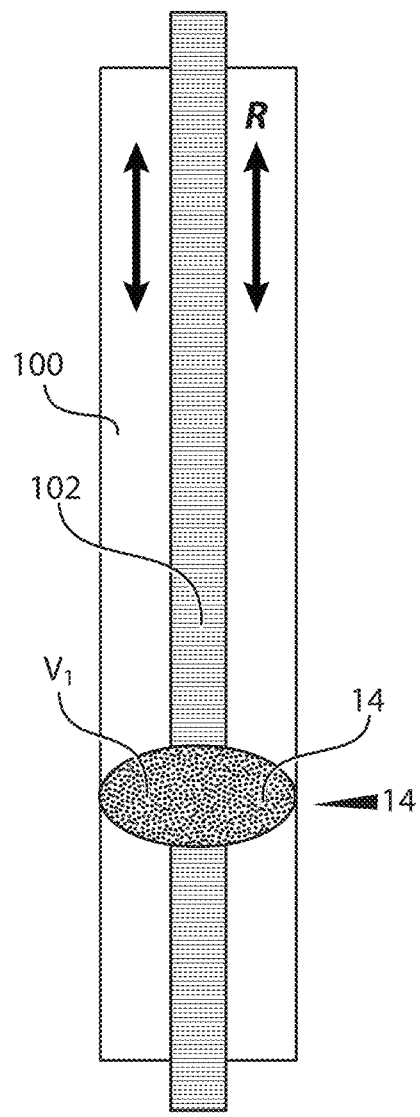
FIG. 5A is a schematic representation of a small volume injected into a neuraxis of a patient.
Figure 5B:
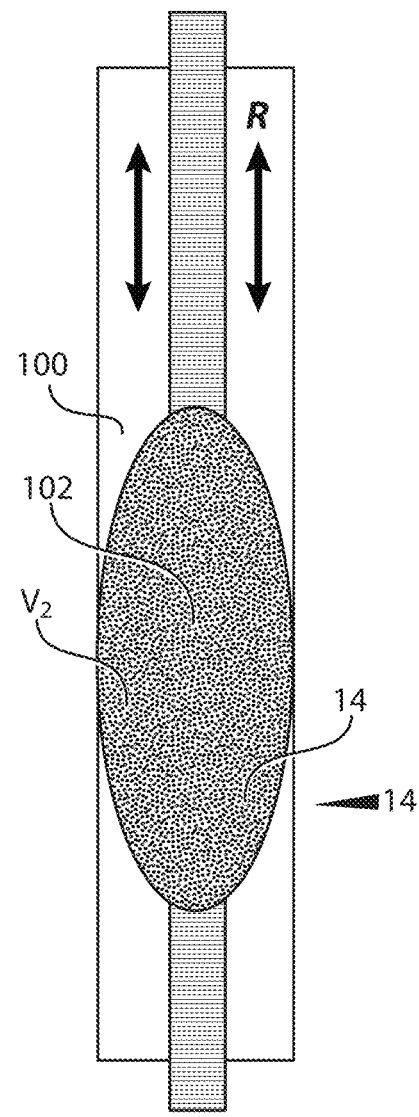
FIG. 5B is a schematic representation of a large volume injected into a neuraxis of a patient.

FIGS. 5A and 5B illustrate the effect of bolus volume on the distribution of a compound and/or solution after injection into the CSF of a patient. In the figures, a bolus of solution 12 is injected at injection site 14. In this particular case, the bolus has been injected into the spinal channel 100 which contains CSF as well as the spinal cord 102 extending along the channel. The reciprocating movement of the CSF is indicated by the double-sided arrows R. FIG. 5A illustrates a smaller bolus volume $V_1$ and FIG. 5B illustrates a larger bolus volume $V_2$. As can be seen in the figures, the larger bolus volume $V_2$ occupies a larger space within the spinal channel 100 and extends further along the length of the spinal channel than the smaller bonus volume $V_1$ when initially injected. Consequently, increasing bolus volumes correspond to larger lengths of a spinal channel, and thus neuraxis, of a patient being initially exposed to a solution upon injection. Additionally, since the larger bolus volumes will extend further along the spinal channel and neuraxis of the patient when first injected, the times needed to further distribute the solution to a desired target location is correspondingly reduced.

Examples: Effects of Volume and Time Varying Force on Compound Distribution

Figure 6:
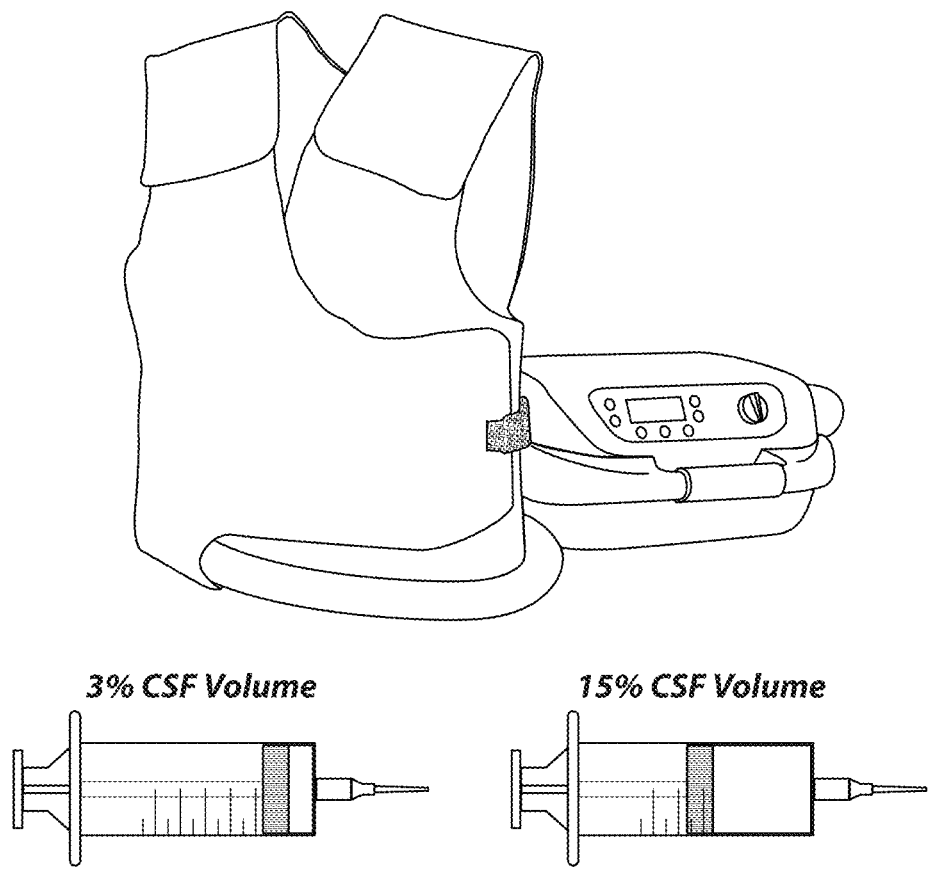
FIG. 6 is an image of a respiratory therapy vest and injection volumes used in the testing of Cynomolgus monkeys.

The ability of a time varying force applied to the torso of a patient and increased bolus volumes to enhance CNS exposure of intrathecally injected compounds was tested in cynomolgus monkeys. Specifically, live whole animal positron emission tomography (PET) imaging was used to monitor the distribution of intrathecally injected $^{64}$Cu-DOTA given as a compound surrogate. This approach allowed the direct imaging of the impact of the convective force on compound spread in CSF and the exposure of the primate CNS to the compound. During the experiments, Cynomolgus monkeys were given a lumbar intrathecal injection of $^{64}$Cu-DOTA in a volume of either 0.36 ml (about 3% of the total CSF volume) or 1.86 ml (about 15% of the total CSF volume), see FIG. 6. The 3% total CSF volume was chosen to mimic a typical lumbar intrathecal injection volume of about 5 ml that is used clinically. Following lumbar intrathecal injection, the animals were placed in a respiratory vest for 20 minutes. The vest was turned on for 20 minutes only for those animals in which the effect of the time varying force enhanced convection was tested. Animals wearing the vest without activating the time varying force feature served as controls. Animals were then imaged with PET scanning for a time window of 30-60 min post dosing. Representative results from these experiments are shown in FIGS. 7A-7D.

Figure 7A:
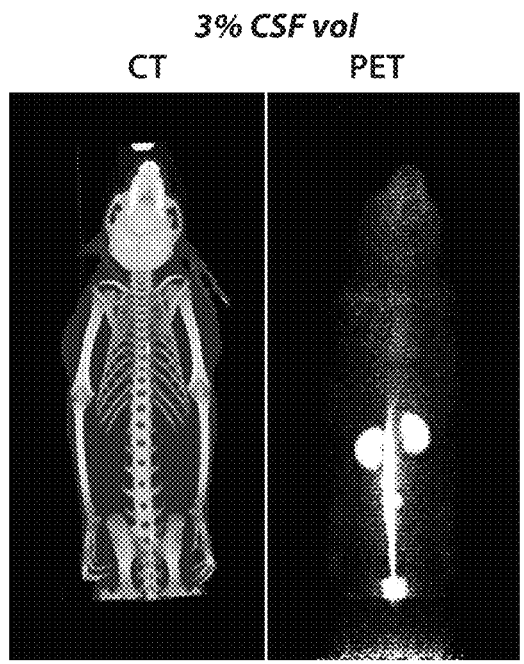
FIG. 7A is an image showing compound concentration distribution along a neuraxis of a monkey for an intrathecal injection at 3% of the cerebrospinal fluid volume.
Figure 7B:
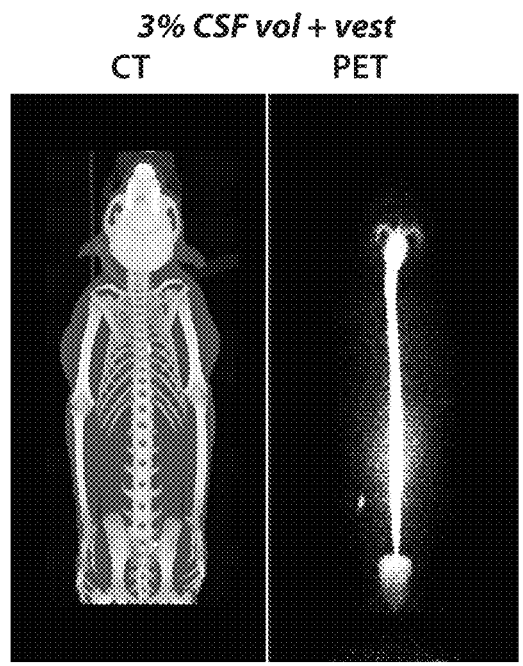
FIG. 7B is an image showing compound concentration distribution along a neuraxis of a monkey for an intrathecal injection at 3% of the cerebrospinal fluid volume with a time varying force applied by a respiratory therapy vest.

As illustrated in FIG. 7A, for animals that did not have the vest turned on, lumbar intrathecal $^{64}$Cu-DOTA given at 3% CSF volume typically only reached the lower thoracic spinal cord during the imaging period. However, when the respiratory vest was turned on following the same dose, the entire spinal cord, and brainstem displayed exposure to $^{64}$Cu-DOTA, see FIG. 7B. Therefore, the mechanical percussive action of the vest led to compound reaching other structures located more rostrally within the skull, including the supracellar cistern and the lateral sulcus of the brain as compared to only reaching the lower thoracic spinal cord.

Figure 7C:
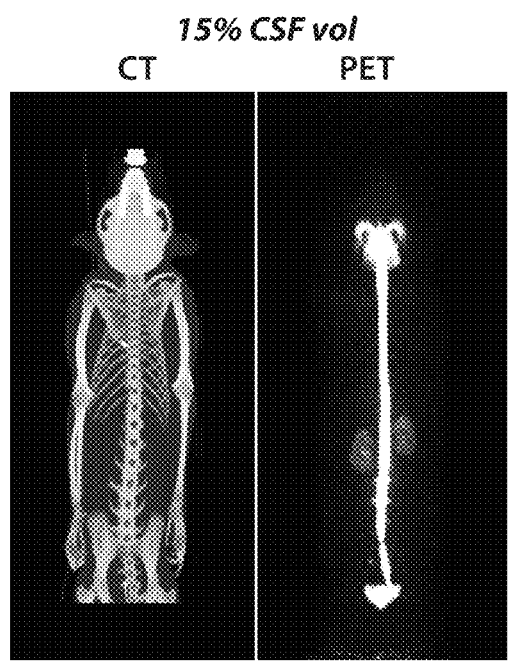
FIG. 7C is an image showing compound concentration distribution along a neuraxis of a monkey for an intrathecal injection at 15% of the cerebrospinal fluid volume.
Figure 7D:
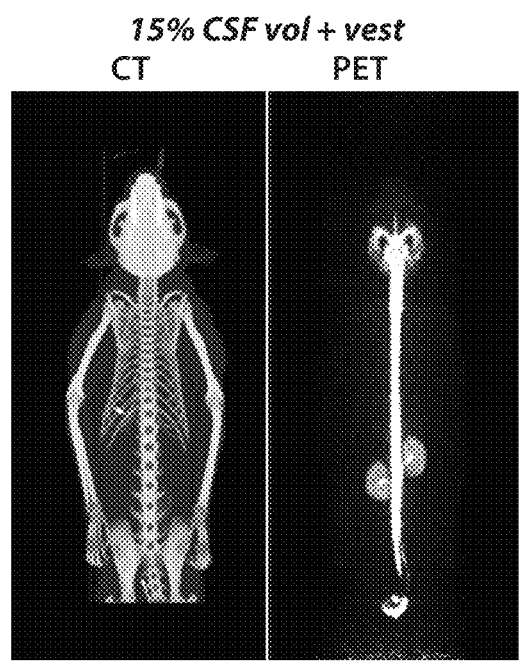
FIG. 7D is an image showing compound concentration distribution along a neuraxis of a monkey for an intrathecal injection at 15% of the cerebrospinal fluid volume with a time varying force applied by a respiratory therapy vest.

When the same dose of lumbar intrathecal $^{64}$Cu-DOTA was given in a bolus equaling 15% CSF volume without the vest being activated, the CNS exposure was markedly improved over the 3% CSF volume dose showing exposure over the entire spinal cord and portions of the brainstem, see FIG. 7C. Thus, a larger bolus volume provided enhanced compound distribution that is comparable to those results obtained using a smaller bolus volume with a time varying force applied to the torso of the subject. The greatest rostral spread of $^{64}$Cu-DOTA was observed when the increased bolus volume of 15% CSF volume was combined with the time varying forces provided by the vest. Therefore, it appears that the effects from applying a time varying force to the torso of a subject and increased bolus volumes are additive to one another.

The above results demonstrate the principle of applying a time varying force to a torso of a patient and the use of increased bolus volumes to improve the distribution of compounds within the neuraxis of a patient.

Example: Cell Targeting Tracer Molecules

Two different probes including different isotopes were injected via a single 20 ml bolus into rodents and then imaged at different energies. FIG. 8A depicts a structure of the first non-cell penetrating probe $^{111}$In-DTPA. FIG. 8B depicts a structure of the second mitochondria targeting probe $^{99m}$Tc-Sestamibi. The bolus was injected into the lumbar cistern and the cisterna magna to help distinguish uptake into interstitial spaces versus uptake into intracellular compartments, see FIG. 8C. As expected, the mitochondria targeting probe, which has high local tissue affinity showed very little distribution along the CNS. However, the non-cell penetrating probe showed distribution from the injection site towards the head of the rodent along the CNS as expected due to convective mixing forces of the CSF facilitating distribution of the non-cell penetrating probe. Consequently, it is apparent that the cell affinity of a compound for the structures and tissue within the CNS should be considered when determining the optimal parameters, such as injection site, bolus volume, and the applied forces, needed to ensure a compound reaches a desired target site.

Example: Bolus Volume Effect

Similar to the above example, two different probes including different isotopes were injected in a single bolus. The two probes again included a non-cell penetrating probe $^{111}$In-DTPA and a mitochondria targeting probe $^{99m}$Tc-Sestamibi. The same amount of each probe was used in each injected bolus. However, the total bolus volumes for the separate injections were 20 μl and 30 μl followed by a 40 μl saline flush. The boluses were injected intrathecally into rodents and the concentration of the two probes was monitored at the lumbar, thoracic, and cervical regions.

Figure 9A:
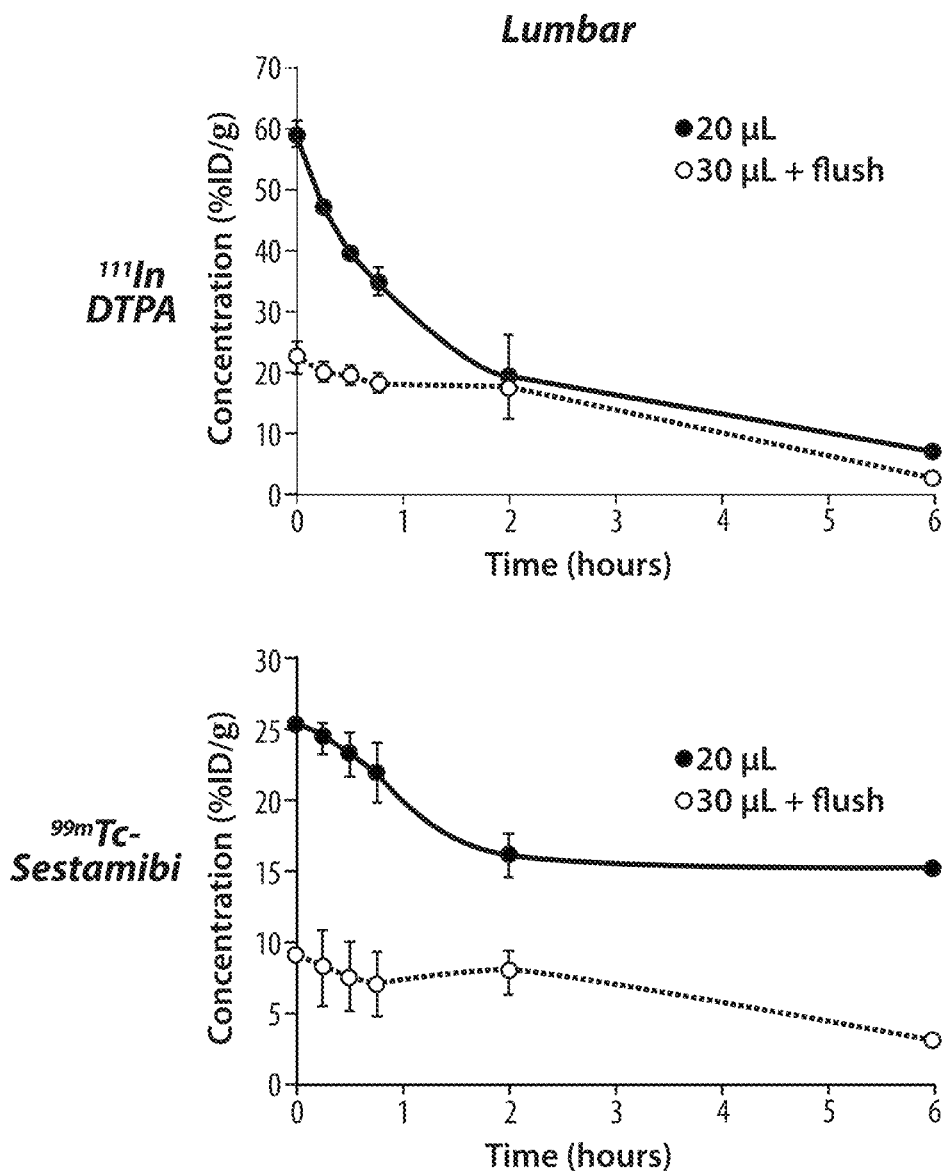
FIG. 9A presents graphs of the concentration of In-DTPA and Tc-Sestamibi in the lumbar region versus time for intrathecal injections made using different bolus volumes.
Figure 9B:
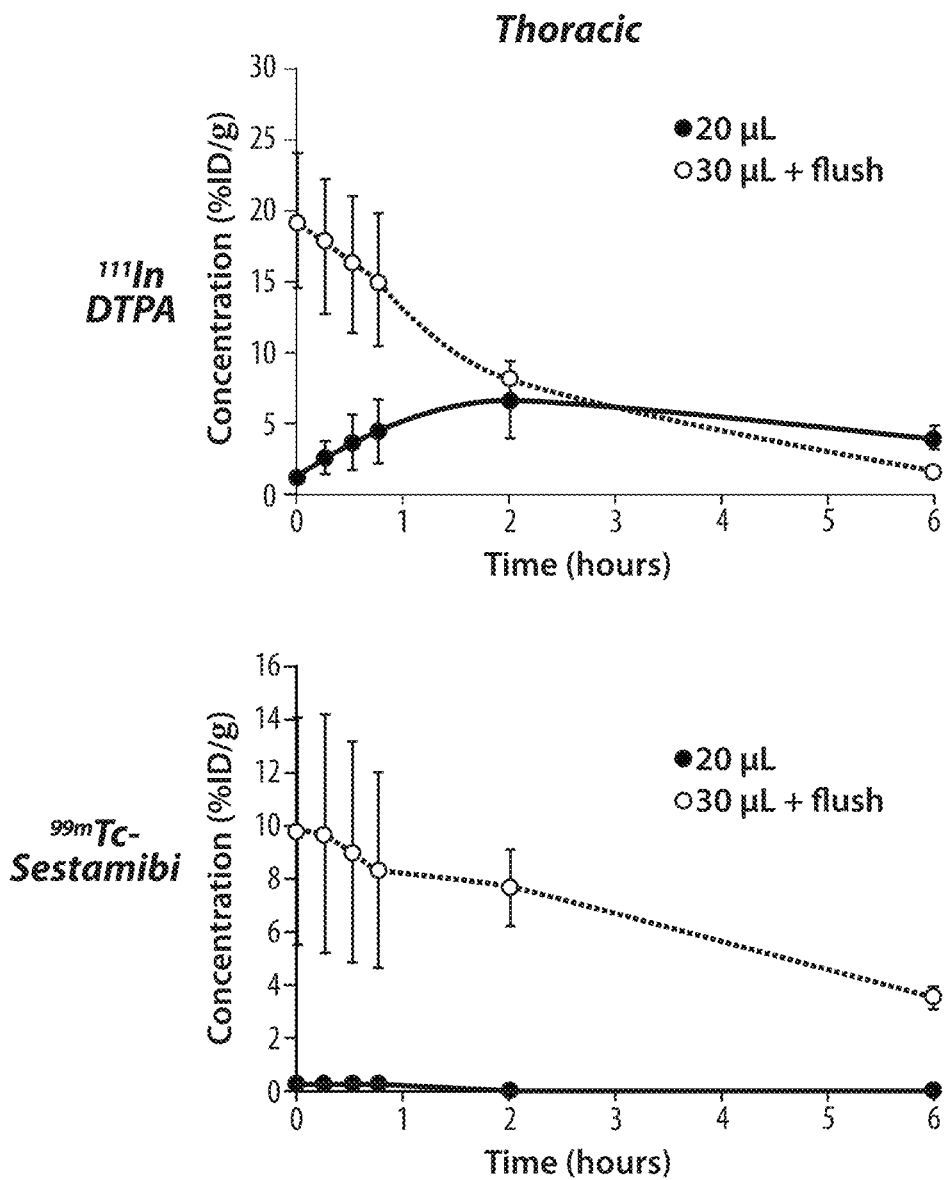
FIG. 9B presents graphs of the concentration of In-DTPA and Tc-Sestamibi in the thoracic region versus time for intrathecal injections made using different bolus volumes.
Figure 9C:
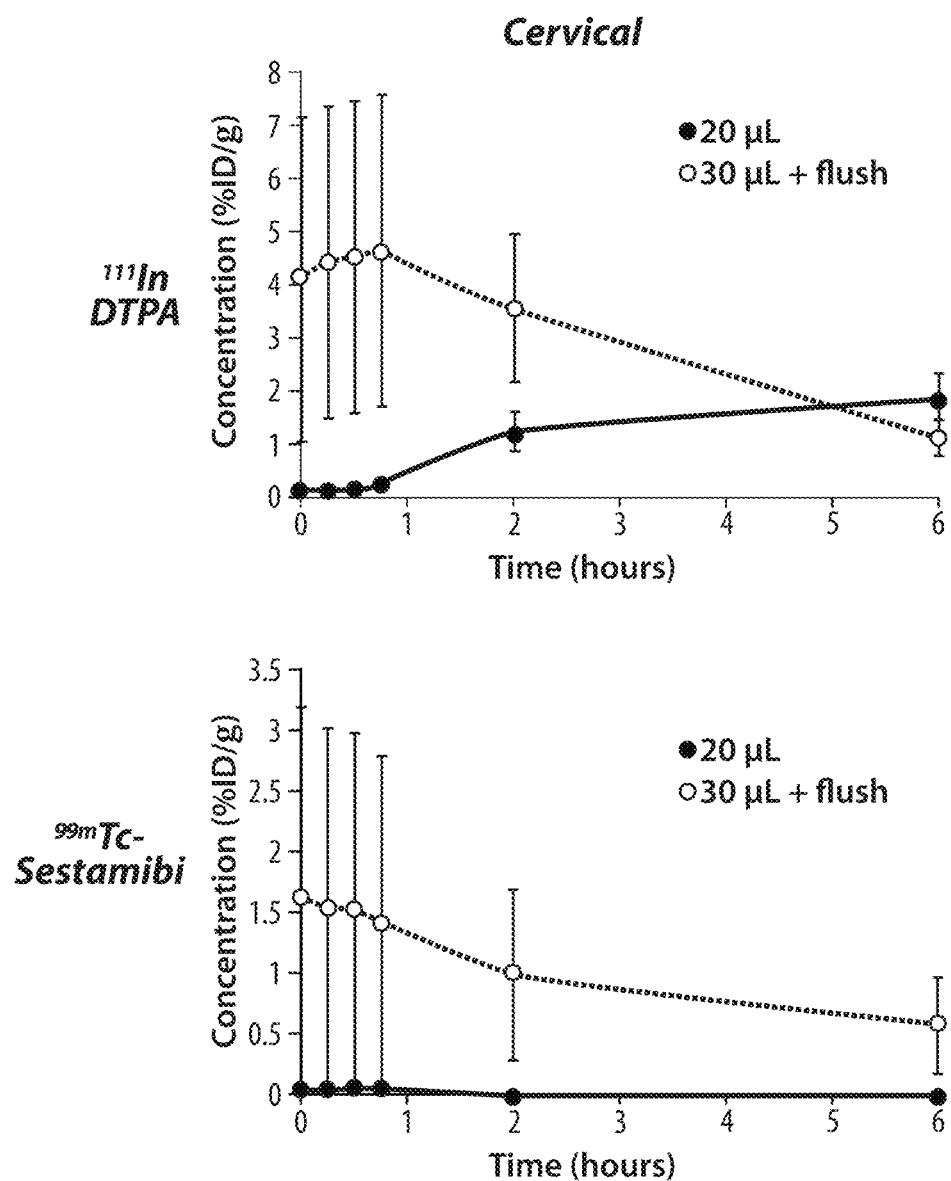
FIG. 9C presents graphs of the concentration of In-DTPA and Tc-Sestamibi in the cervical region versus time for intrathecal injections made using different bolus volumes.

As can be seen in FIGS. 9A-9C, the 20 μl bolus injection has an initially high concentration of $^{111}$In-DTPA and $^{99m}$Tc-Sestamibi in the lumbar region, i.e. the injection site, that decreases over time. As expected, the non-cell penetrating probe shows a larger concentration decrease over time in this region. Correspondingly, the concentration of $^{111}$In-DTPA increases over time in both the thoracic and cervical regions. In contrast, the concentration of the mitochondria targeting probe, $^{99m}$Tc-Sestamibi, did not increase over this time. Without wishing to be bound by theory, the lack of $^{99m}$Tc-Sestamibi in these regions is likely due to it becoming entrapped intracellularly in the lumbar spinal cord.

In contrast to the above, the 30 μl bolus with 40 μl additional volume results in a reduced concentration of both probes in the lumbar region at initial injection as compared to the 20 μl bolus. However, the concentration of both probes in the thoracic and cervical regions are drastically increased with the higher bolus volumes. These initial concentrations also decrease slightly in each region as the probes become further distributed within the CNS of the rodents.

The above results make it clear that the increased bolus volume resulted in increased distribution of both the non-cell targeting probe and mitochondria targeting probe throughout the lumbar, thoracic, and cervical regions as compared to the smaller bolus which was only capable of distributing both probes to the lumbar region. This illustrates the effectiveness of larger bolus volumes for enhancing the distribution of a desired compound along the CNS and neuraxis of a patient.

Figure 10A:
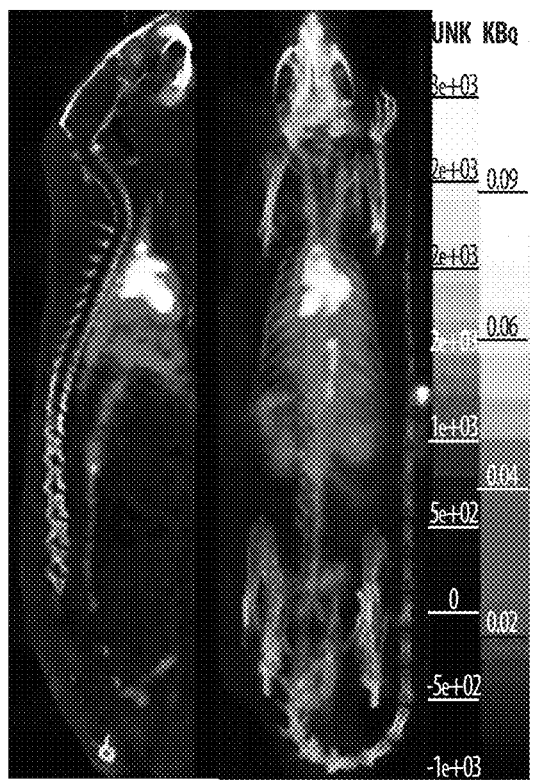
FIG. 10A-10B are SPECT scans of the concentrations of $^{123}$I-Albumin after intravenous injection.
Figure 10B:
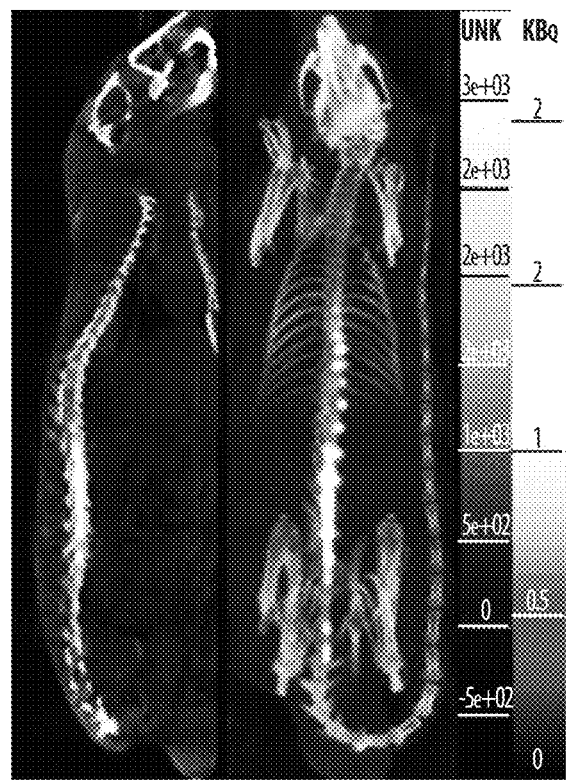
Figures 11A, 11B, 11C, 11D:
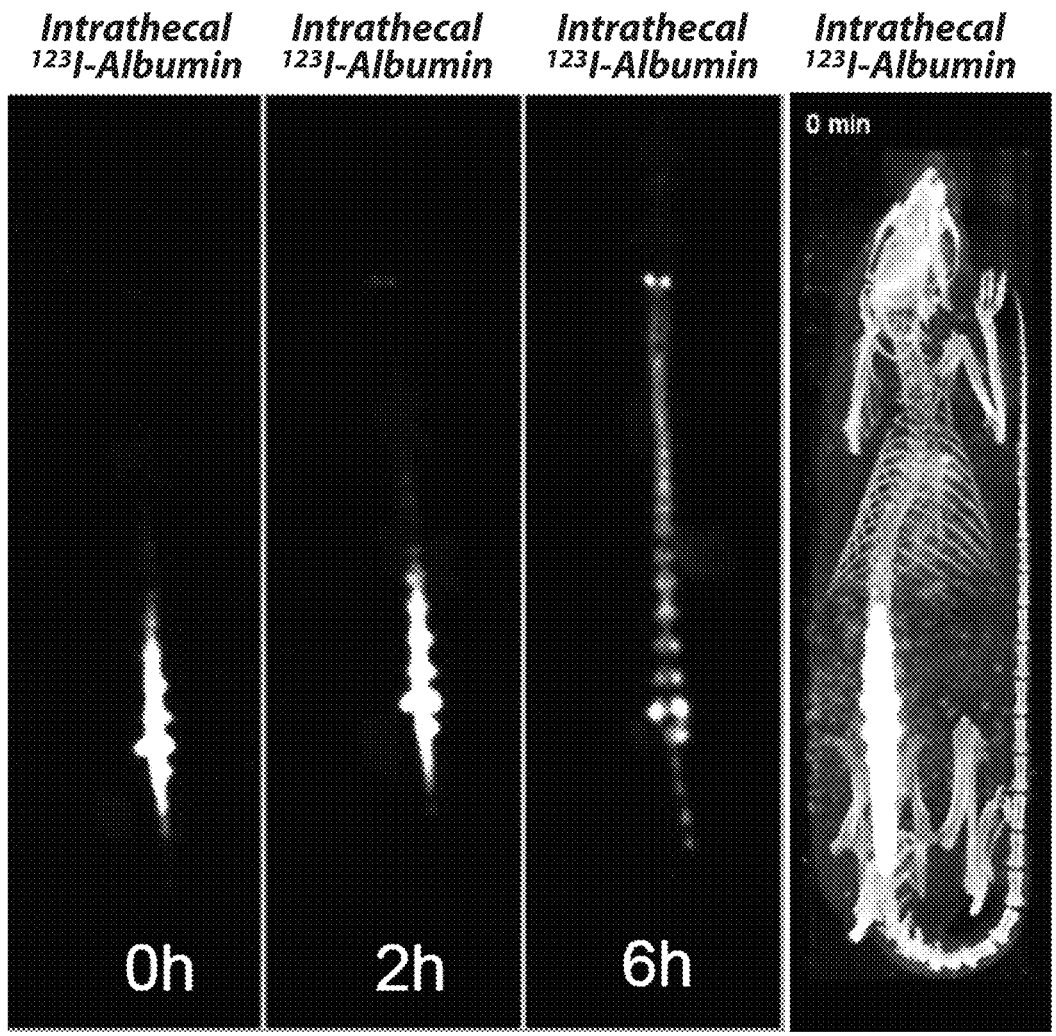
FIGS. 11A-11D are scans of the concentrations of $^{123}$I-Albumin after intrathecal injection at different time points.

Example: Intravenous Vs. Intrathecal Injection of Albumin $^{123}$I-Albumin was intravenously and intrathecally injected into a rodent. FIGS. 10A and 10B are scans of the concentration of $^{123}$I-Albumin after intravenous injection. The scans revealed that the albumin is distributed throughout the rodent's body and does not specifically target the CNS of the rodent. In contrast, the intrathecally injected albumin stays relatively localized within the CSF of the rodent as it spreads along the CNS of the rodent. This experiment demonstrates that the convection of molecules within CSF helps to distribute the molecules throughout the CNS for both smaller molecules such as the probes described above as well as larger molecules such as albumin. Therefore, and without wishing to be bound by theory, it does not appear that the molecular weight of a particular compound has a significant effect on its distribution within CSF where convective mixing of the CSF appears to dominate the transport characteristics. Consequently, the application of forces and increased bolus volumes described herein may be used for low molecular weight compounds as well as larger molecular weight compounds.

Example: Probe Distribution Vs. Time for Different Injection Sites

Figure 12A:
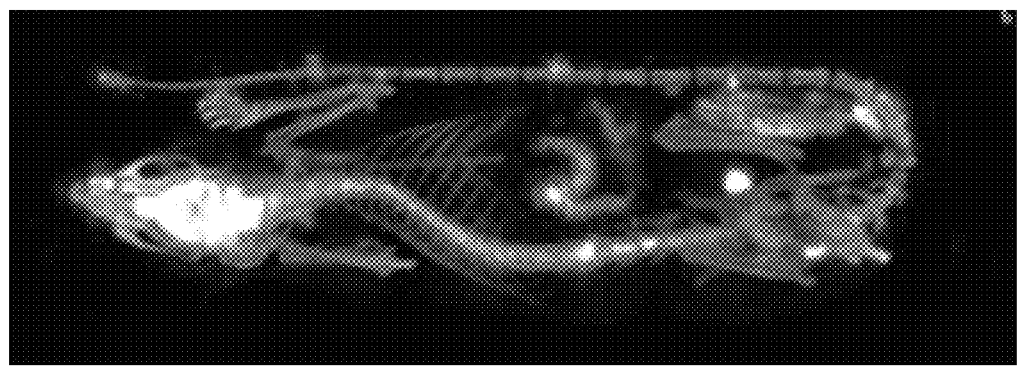
FIG. 12A is a SPECT scan of the concentration of $^{123}$I-Albumin after cisternal injection.
Figure 12B:
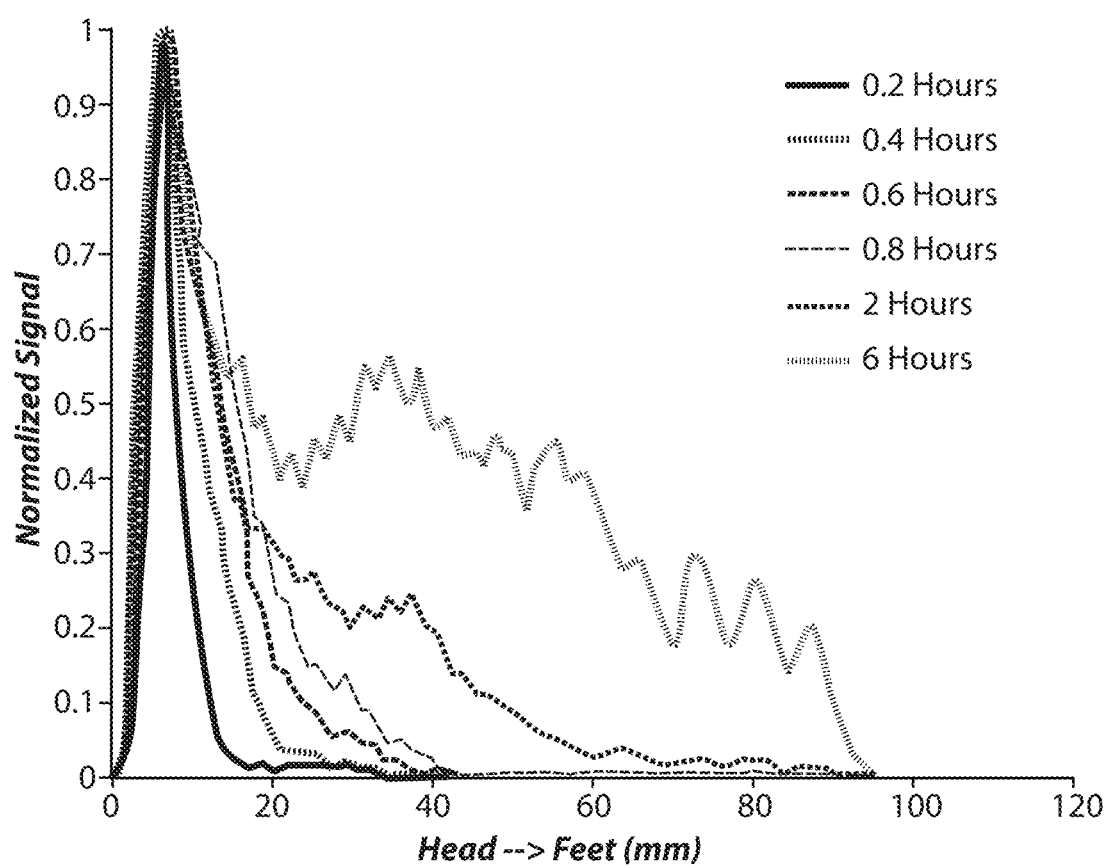
FIG. 12B is a graph of the concentration of $^{123}$I-Albumin from the head to the feet at different time points after cisternal injection.
Figure 13A:
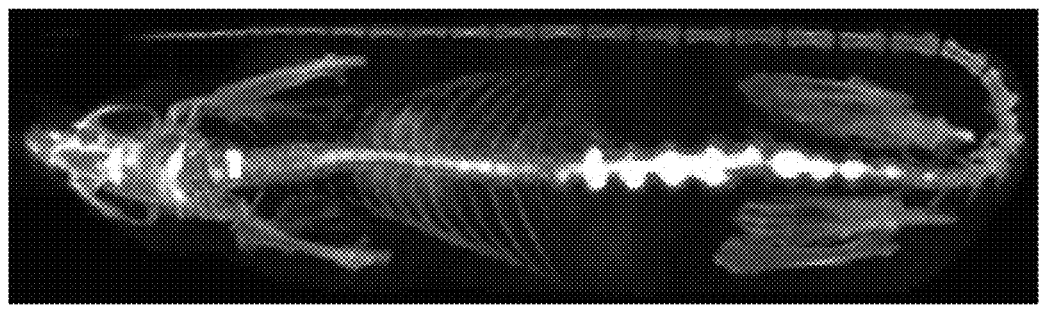
FIG. 13A is a SPECT scan of the concentration of $^{123}$I-Albumin after intrathecal injection.
Figure 13B:
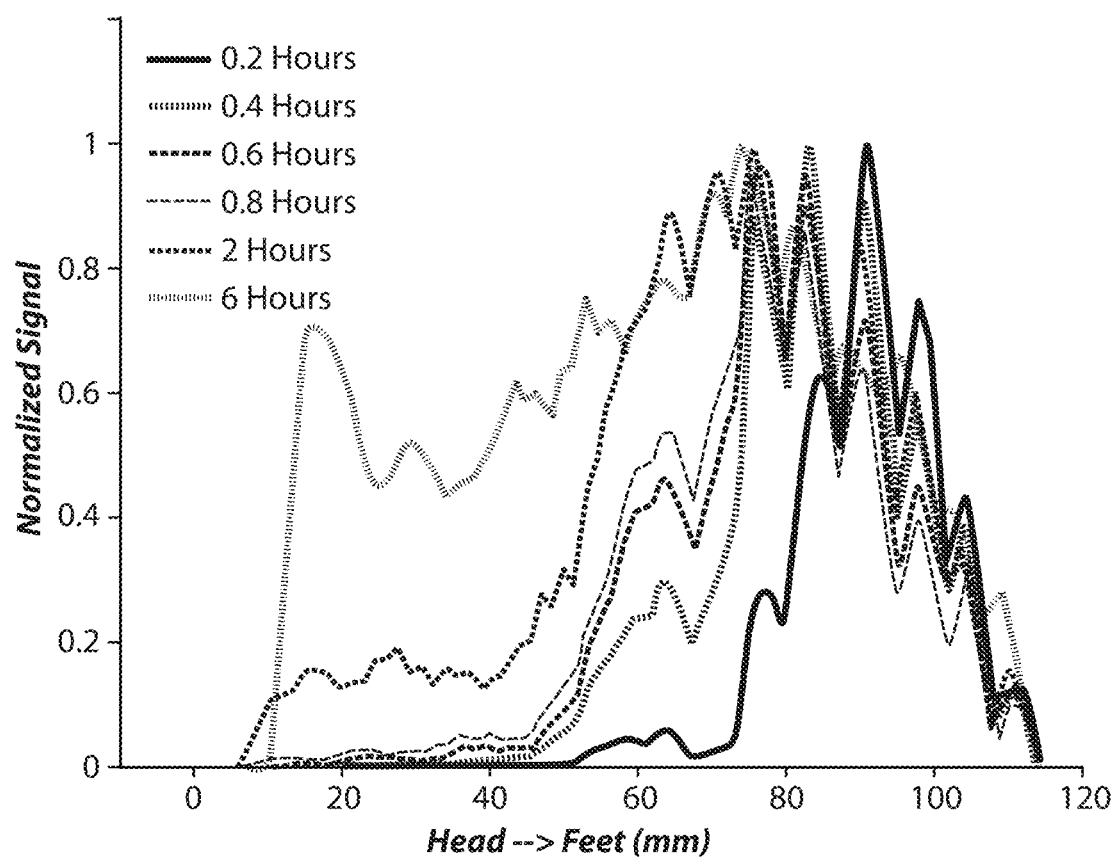
FIG. 13B is a graph of the concentration of [123]I-Albumin from the head to the feet at different time points after intrathecal injection.

FIGS. 12A and 13A show scans of the concentration of $^{123}$I-Albumin after injection into the cisterna magnum and lumbar cistern into a rodent respectively. FIGS. 12B and 13B present graphs of the concentration of $^{123}$I-Albumin from the head to the feet at different time points after cisternal injection and intrathecal injection respectively. After six hours of monitoring, the intrathecal injection shows the more even distribution of albumin from the head to the feet of the rodent. Lymphoseek ([$^{99m}$Tc]DTPA-mannosyl-dextran, Navidea Biopharmaceuticals)

Example: Interconnectivity of CSF and Lymph Nodes

Figure 14A:
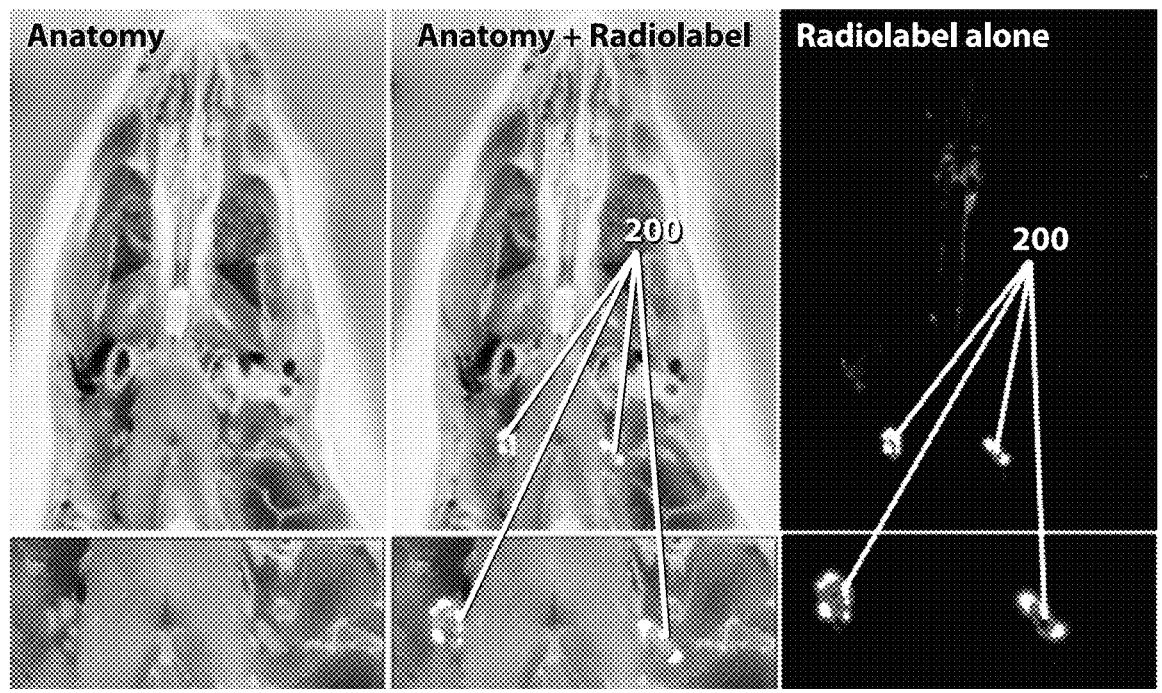
FIG. 14A is a SPECT CT scan showing the presence of an intrathecally injected compound present in the head and neck lymph nodes.
Figure 14B:
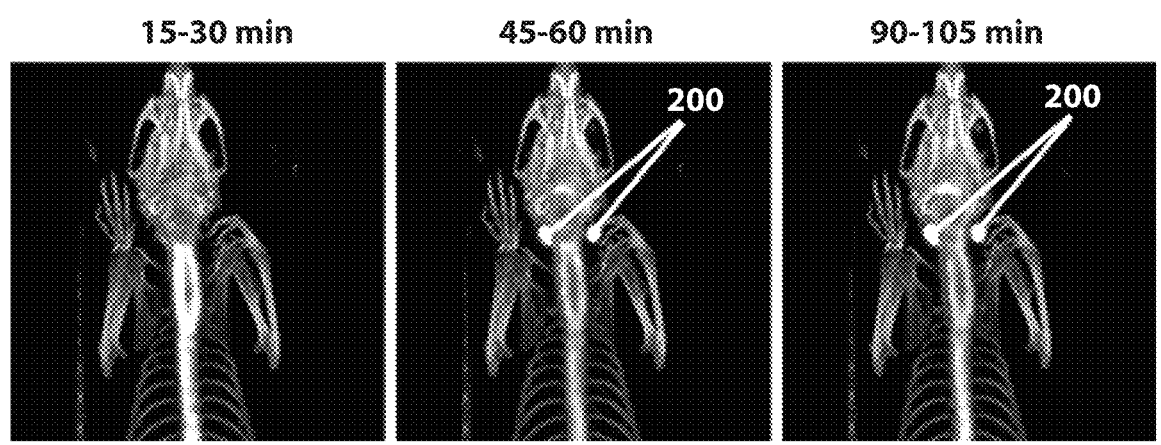
FIG. 14B is a SPECT CT scan showing the presence of an intrathecally injected compound present in the head and neck lymph nodes over a monitored time period of 105 minutes.

Lymphoseek ([$^{99m}$Tc]DTPA-mannosyl-dextran, Navidea Biopharmaceuticals) is a diagnostic agent used to map draining lymph nodes from neoplastic tumors. Lymphoseek was intrathecally injected into a rodent for the first time into a rodent which was then imaged over time. As illustrated in FIGS. 14A and 14B, the intrathecally injected Lymphoseek migrated into the head and neck lymph nodes 200 over the monitored time period of 105 minutes. Consequently, compounds injected directly into CSF may also be used as a distribution route to reach lymph nodes in some applications, particularly those lymphatics involved in immune surveillance of the central nervous system. Additionally, due to the interconnectivity of the CSF and lymph nodes demonstrated by this example, compounds injected into the lymph nodes may also be used to as a distribution route for compounds to the CSF and associated CNS.

Example: Real Time Measurement

Figure 15A:
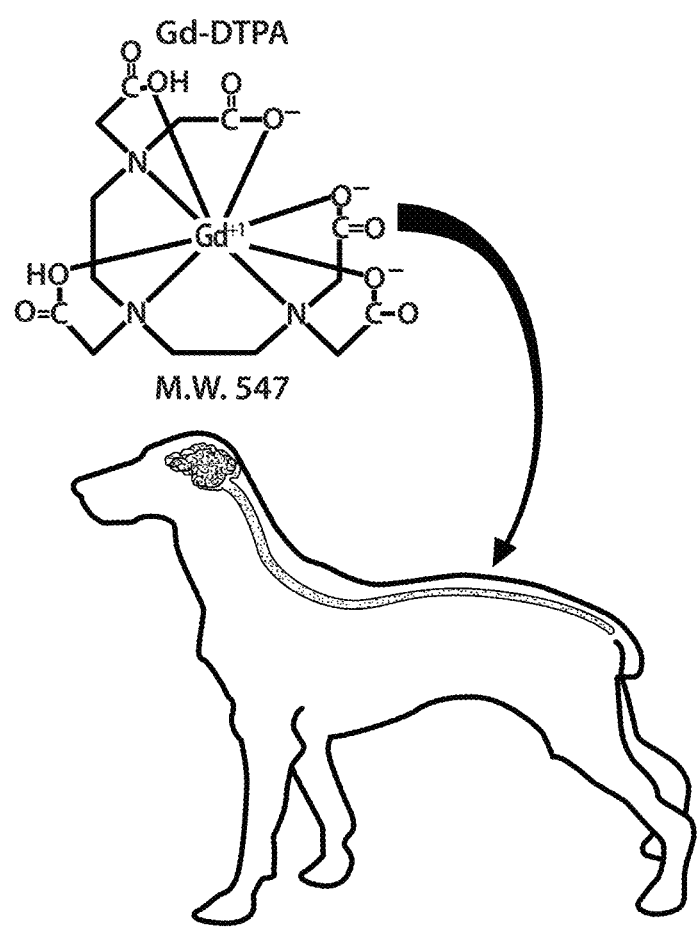
FIG. 15A is a schematic representation of Gd-DTPA being injected into a dog.
Figure 15B:
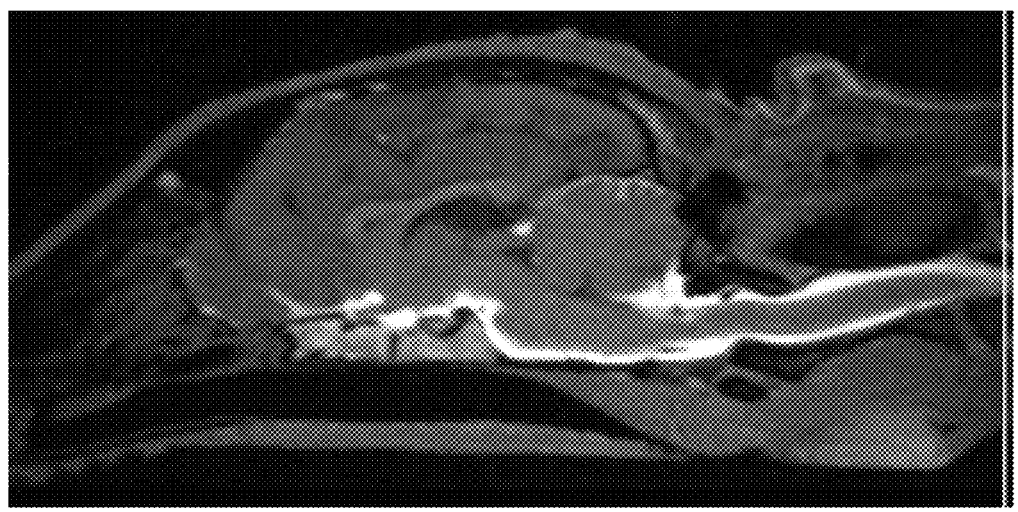
FIG. 15B is a scan showing the presence of Gd-DTPA located in the CSF and interstitial spaces of a dog brain.
Figure 15C:
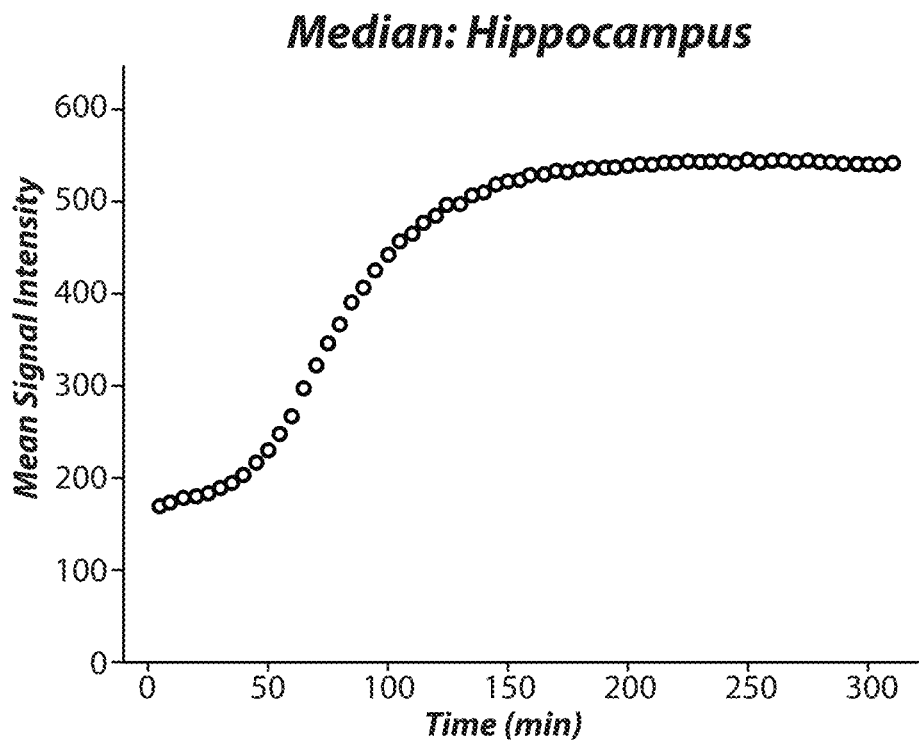
FIG. 15C is a graph of the detected signal intensity over time of Gd-DTPA in the hippocampus.
Figure 15D:
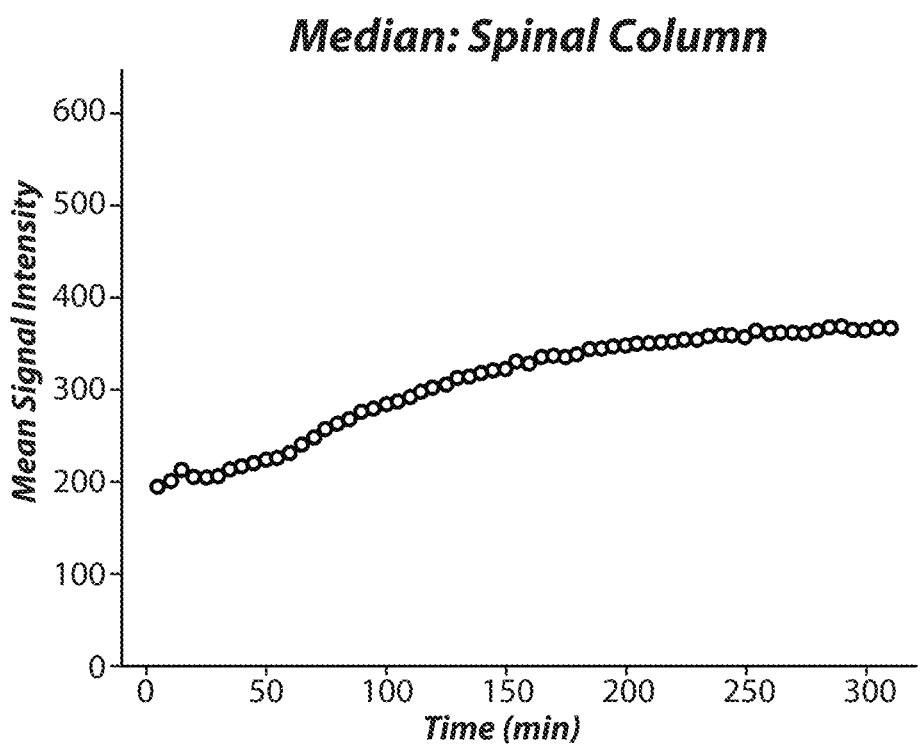
FIG. 15D is a graph of the detected signal intensity over time of Gd-DTPA in the spinal column.
Figure 15E:
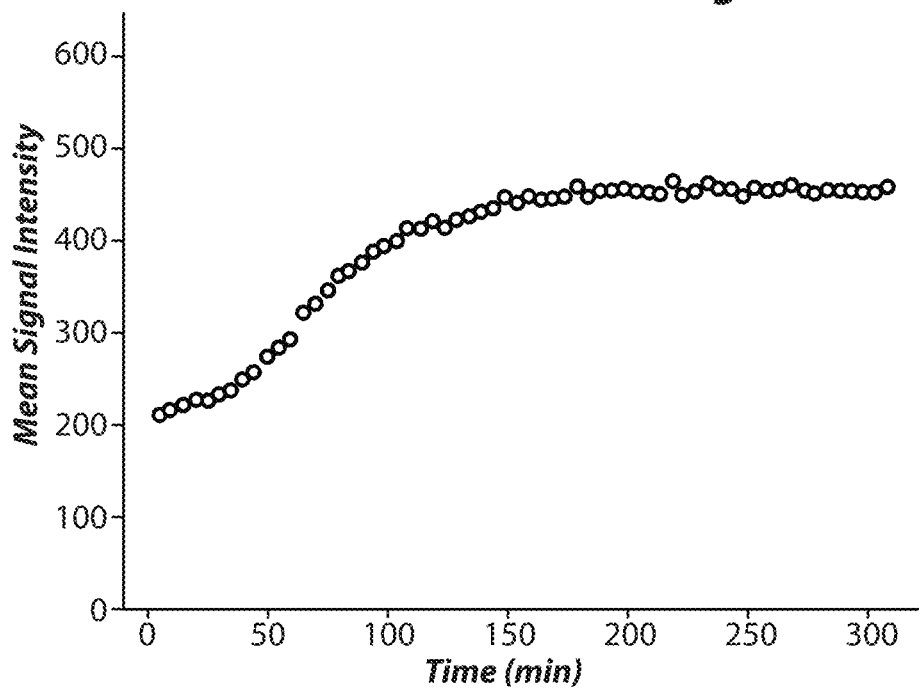
FIG. 15E is a graph of the detected signal intensity over time of Gd-DTPA in the substantia nigra.
Figure 15F:
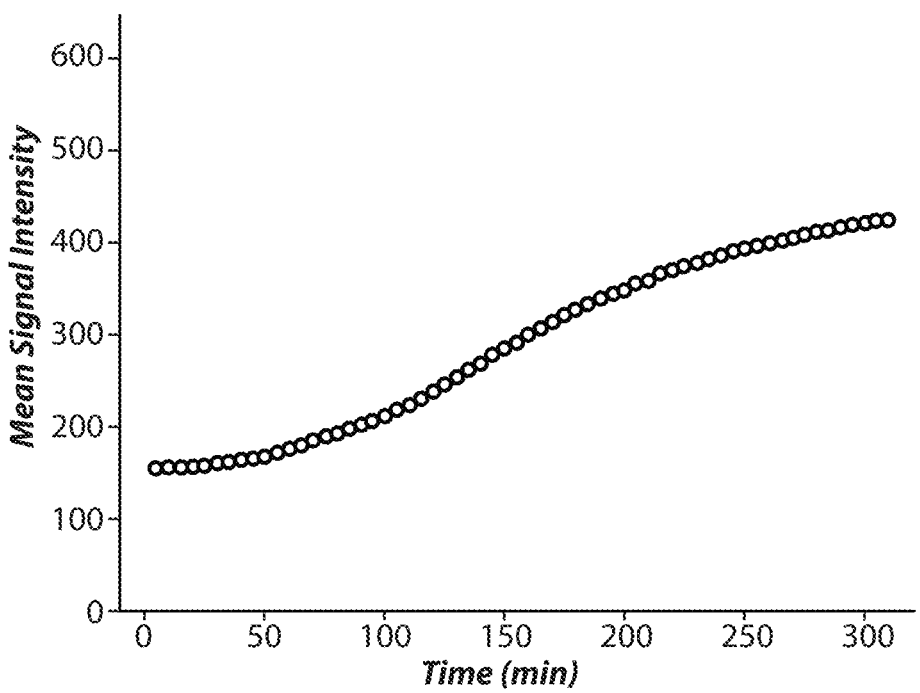
FIG. 15F is a graph of the detected signal intensity over time of Gd-DTPA in the cortex.
Figure 15G:
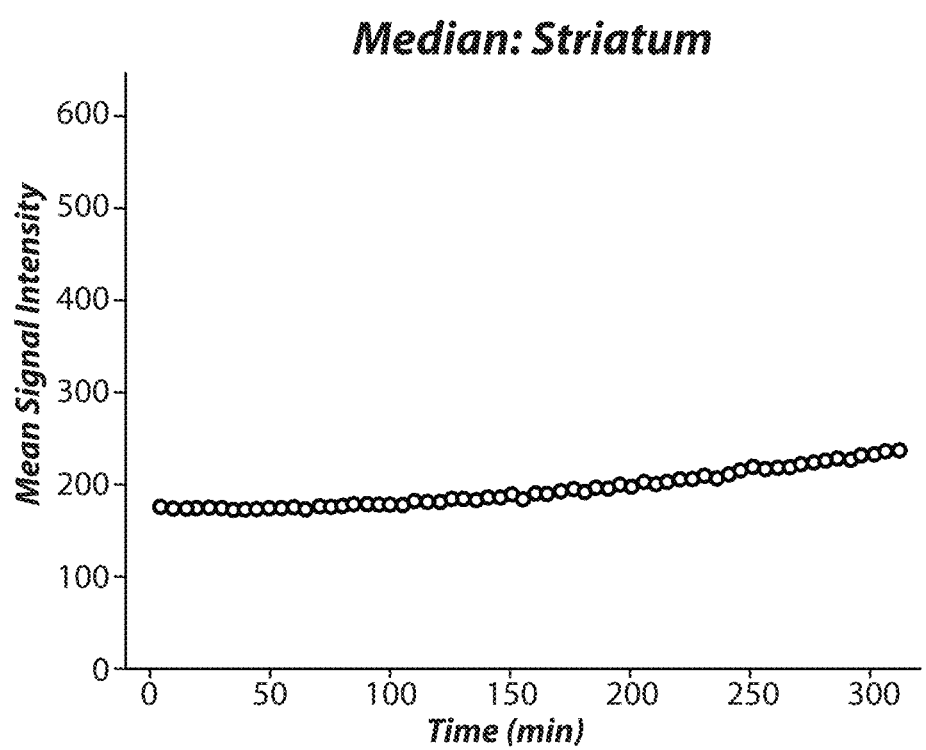
FIG. 15G is a graph of the detected signal intensity over time of Gd-DTPA in the striatum.

FIG. 15A shows a schematic diagram of Gd-DTPA being intrathecally injected into a dog. For this experiment, an adult male two-year-old beagle was intrathecally injected at the L4-L5 space and live imaging was performed under anesthesia for five hours. As illustrated by FIG. 15B, the Gd-DTPA was not taken up into the cells but instead was located in the interstitial spaces of the brain by traveling from the subarachnoid space along the perivascular spaces.

FIGS. 15C-15G show the signal counts corresponding to the presence of Gd-DTPA over the five hour monitoring period. The various monitored locations included the hippocampus, spinal column, substantia nigra, cortex, and striatum. Each location exhibited an increase in the measured signal intensity over time. These results validate the concept of monitoring the presence and/or concentration of a desired compound, such as a marked compound and/or solution, at a target location using sensors to make these types of real time measurements.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method for dispersing a compound within an intrathecal neuraxis of a patient, the method comprising:
applying a force to a torso of a patient to enhance convection of cerebrospinal fluid that includes an effective amount of a compound to enhance dispersion of the compound.

2. The method of claim 1, wherein the compound is a therapeutic compound, a diagnostic compound, or a combination thereof.

3. The method of claim 1, wherein the force includes a gradient along a length of the body.

4. The method of claim 1, further comprising injecting the compound into the cerebrospinal fluid of the patient.

5. The method of claim 1, wherein the force is applied for a period of time sufficient to enhance distribution of the compound in the cerebrospinal fluid.

6. The method of claim 1, wherein a total force change, frequency, wave form, and/or wave/pause sequences of the force is selected to enhance convection of the cerebrospinal fluid.

7. The method of claim 1, wherein the force is a static force.

8. The method of claim 1, wherein the force is a dynamic force.

9. The method of claim 8, wherein a total force change of the force is between or equal to about 0 and 1 PSI.

10. The method of claim 9, wherein a frequency of the force is between or equal to about 5 Hz and 25 Hz.

11. The method of claim 1, wherein the force is applied substantially normal to the torso of the patient.

12. The method of claim 1, wherein applying the force further comprises sequentially applying the force to a first location on the torso and a second location on the torso.

13. The method of claim 1, further comprising sensing a concentration of the compound at a target site.

14. The method of claim 13, further comprising ending the application of the force when the sensed concentration of the compound at the target site is greater than a threshold concentration.

15. The method of claim 1, wherein applying the force further comprises applying the force to the torso of the patient sufficient to enhance convection of lymph that includes an effective amount of the compound contained in a lymph node to enhance dispersion of the compound.

16. The method of claim 15, wherein the compound is a therapeutic compound, a diagnostic compound, or a combination thereof.

17. The method of claim 15, wherein the force includes a gradient along a length of the body.

18. The method of claim 15, further comprising injecting the compound into the cerebrospinal fluid of the patient.

19. The method of claim 15, wherein the force is applied for a period of time sufficient to enhance distribution of the compound from the lymph node to the cerebrospinal fluid of the patient.

20. The method of claim 15, wherein a total force change, frequency, wave form, and/or wave/pause sequences of the force is selected to enhance convection of the lymph.

21. The method of claim 15, wherein the force is a static force.

22. The method of claim 15, wherein the force is a dynamic force.

23. The method of claim 22, wherein a total force change of the force is between or equal to about 0 and 1 PSI.

24. The method of claim 23, wherein a frequency of the force is between or equal to about 5 Hz and 25 Hz.

25. The method of claim 15, wherein the force is applied substantially normal to the torso the patient.

26. The method of claim 25, wherein applying the force further comprises sequentially applying the force to a first location on the torso and a second location on the torso.

27. The method of claim 15, further comprising sensing a concentration of the compound at a target site in the central nervous system.

28. The method of claim 27, further comprising ending the application of the force when the sensed concentration of the compound at the target site in the central nervous system is greater than a threshold concentration.

29. The method of claim 1, the method further comprising injecting a bolus including the compound into the cerebrospinal fluid of a patient, wherein a volume of the bolus is between or equal to about 5% and 30% of a total volume of the cerebrospinal fluid of the patient.

30. The method of claim 29, wherein the compound is a therapeutic compound, a diagnostic compound, or a combination thereof.

31. The method of claim 29, wherein the force includes a gradient along a length of the body.

32. The method of claim 29, wherein the force is applied for a period of time sufficient to enhance distribution of the compound in the cerebrospinal fluid.

33. The method of claim 29, wherein a total force change, frequency, wave form, and/or wave/pause sequences of the force is selected to enhance convection of the cerebrospinal fluid.

34. The method of claim 29, wherein the force is a static force.

35. The method of claim 29, wherein the force is a dynamic force.

36. The method of claim 35, wherein a total force change of the force is between or equal to about 0 and 1 PSI.

37. The method of claim 36, wherein a frequency of the force is between or equal to about 5 Hz and 25 Hz.

38. The method of claim 29, wherein the force is applied substantially normal to the torso the patient.

39. The method of claim 29, further comprising determining the total volume of the cerebrospinal fluid of the patient to determine the volume of the bolus prior to injection.

40. The method of claim 29, wherein injecting the bolus further comprises injecting the bolus into a lumbar cistern of the patient.

41. The method of claim 29, wherein applying the force further comprises sequentially applying the force to a first location on the torso and a second location on the torso.

42. The method of claim 29, further comprising sensing a concentration of the compound at a target site.

43. The method of claim 42, further comprising ending the application of the force when the sensed concentration of the compound at the target site is greater than a threshold concentration.

* * * * *